US012559556B1

(12) United States Patent
Liu et al.

(10) Patent No.: US 12,559,556 B1
(45) Date of Patent: Feb. 24, 2026

(54) BCMA × CD3 T BISPECIFIC CELL ENGAGER

(71) Applicant: CHONGQING GENRIX BIOPHARMACEUTICAL CO., LTD., Chongqing (CN)

(72) Inventors: Zhigang Liu, Beijing (CN); Shunan Wan, Beijing (CN); Yulan Liu, Beijing (CN); Xiaobo Hao, Beijing (CN); Junjie Hu, Beijing (CN); Jingjing Guo, Beijing (CN)

(73) Assignee: Chongqing Genrix Biopharmaceutical Co., Ltd., Chongqing (CN)

( * ) Notice: Subject to any disclaimer, the term of this patent is extended or adjusted under 35 U.S.C. 154(b) by 0 days.

(21) Appl. No.: 19/252,926

(22) Filed: Jun. 27, 2025

Related U.S. Application Data

(60) Provisional application No. 63/824,363, filed on Jun. 16, 2025.

(51) Int. Cl.
C07K 16/28 (2006.01)

(52) U.S. Cl.
CPC ...... C07K 16/2809 (2013.01); C07K 16/2878 (2013.01); *C07K 2317/31* (2013.01); *C07K 2317/41* (2013.01); *C07K 2317/73* (2013.01); *C07K 2317/92* (2013.01)

(58) Field of Classification Search
None
See application file for complete search history.

(56) References Cited

U.S. PATENT DOCUMENTS

2023/0212287 A1* 7/2023 Liu .................... C07K 16/2878
424/136.1

FOREIGN PATENT DOCUMENTS

CN 111269315 A * 6/2020 ......... C07K 16/2809

OTHER PUBLICATIONS

ClinicalTrial.gov Study NCT06566547, version 1, Retrieved online from: <URL:https://clinicaltrials.gov/study/NCT06566547?limit=10 &sort=@relevance&intr=GR1803&rank=4&tab=history&a=1#version-content-panel> [retrieved on Aug. 18, 2025], Aug. 20, 2024.*
ClinicalTrials.gov Study NCT06952075, Retrieved online from: <URL:https://clinicaltrials.gov/study/NCT06952075?limit=10&sort= @relevance&intr=GR1803&rank=3&tab=table> [retrieved on Aug. 18, 2025], Apr. 30, 2025.*
Li et al., Pharmacological characterization of GR1803, a novel BCMA × CD3 bispecific antibody for multiple myeloma treatment, Preprint from Research Square, Retreived from <URL:https://doi.org/10.21203/rs.3.rs-1448287/v1> [retrieved on Aug. 18, 2025], Reserach Square, 20 pages, Mar. 24, 2022.*
PubChem substantce ID: 507431977, Velinotamig, Retrieved online from: <URL:https://pubchem.ncbi.nlm.nih.gov/substance/507431977> [retrieved on Aug. 18, 2025], Mar. 11, 2025.*
Jin et al., A Phase I Monotherapy Study Assessing the Safety and Efficacy of GR1803, a BCMA×CD3 Bispecific Antibody, in Patients With Relapsed/Refractory Multiple Myeloma, EHA Library. Jin J Jun. 13, 2024; 421025; p. 961, May 14, 2024.*
Brinkmann et al., The making of bispecific antibodies, MABS, 9(2):182-212, 2017.*
Chen et al., Fusion protein linkers: Property, design and functionality, Adv. Drug Delivy Rev. 65(10):1357-1369, Oct. 2013.*

* cited by examiner

*Primary Examiner* — Claire Kaufman
(74) *Attorney, Agent, or Firm* — Malaika D. Tyson; Lathrop GPM LLP

(57) ABSTRACT

A bispecific antibody, which comprises an antigen-binding portion against human CD3E and an antigen-binding portion against human BCMA.

27 Claims, 4 Drawing Sheets

Specification includes a Sequence Listing.

SEQUENCE LISTING

```
Sequence total quantity: 43
SEQ ID NO: 1              moltype = AA  length = 5
FEATURE                   Location/Qualifiers
source                    1..5
                          mol_type = protein
                          organism = synthetic construct
```

```
SEQUENCE: 1
GYGMH                                                                    5

SEQ ID NO: 2            moltype = AA   length = 17
FEATURE                 Location/Qualifiers
source                  1..17
                        mol_type = protein
                        organism = synthetic construct
SEQUENCE: 2
VIWFDGSRKY YVDSVKG                                                        17

SEQ ID NO: 3            moltype = AA   length = 9
FEATURE                 Location/Qualifiers
source                  1..9
                        mol_type = protein
                        organism = synthetic construct
SEQUENCE: 3
QMGYWHFGL                                                                 9

SEQ ID NO: 4            moltype = AA   length = 11
FEATURE                 Location/Qualifiers
source                  1..11
                        mol_type = protein
                        organism = synthetic construct
SEQUENCE: 4
RASQSISNYL T                                                             11

SEQ ID NO: 5            moltype = AA   length = 7
FEATURE                 Location/Qualifiers
source                  1..7
                        mol_type = protein
                        organism = synthetic construct
SEQUENCE: 5
EASSRPS                                                                   7

SEQ ID NO: 6            moltype = AA   length = 9
FEATURE                 Location/Qualifiers
source                  1..9
                        mol_type = protein
                        organism = synthetic construct
SEQUENCE: 6
QQWSRLPVT                                                                 9

SEQ ID NO: 7            moltype = AA   length = 5
FEATURE                 Location/Qualifiers
source                  1..5
                        mol_type = protein
                        organism = synthetic construct
SEQUENCE: 7
NYWMH                                                                     5

SEQ ID NO: 8            moltype = AA   length = 17
FEATURE                 Location/Qualifiers
source                  1..17
                        mol_type = protein
                        organism = synthetic construct
SEQUENCE: 8
ATYRGHSDTY YNQKFKG                                                        17

SEQ ID NO: 9            moltype = AA   length = 12
FEATURE                 Location/Qualifiers
source                  1..12
                        mol_type = protein
                        organism = synthetic construct
SEQUENCE: 9
GAVYAGYDVL DY                                                            12

SEQ ID NO: 10           moltype = AA   length = 121
FEATURE                 Location/Qualifiers
source                  1..121
                        mol_type = protein
                        organism = synthetic construct
SEQUENCE: 10
QVQLVQSGAE VKKPGSSVKV SCKASGYTFT NYWMHWVRQA PGQGLEWMGA TYRGHSDTYY    60
NQKFKGRVTI TADKSTSTAY MELSSLRSED TAVYYCTRGA VYAGYDVLDY WGQGTTVTVS   120
S                                                                        121

SEQ ID NO: 11           moltype = AA   length = 121
FEATURE                 Location/Qualifiers
```

```
source                   1..121
                         mol_type = protein
                         organism = synthetic construct
SEQUENCE: 11
QVQLVQSGAE VKKPGSSVKV SCKASGYTFT NYWMHWVRQA PGQGLEWMGA TYRGHSDTYY      60
NQKFKGRVTI TADKSTSTAY MELSSLRSED TAVYYCTRGA IYDGYDVLDN WGQGTLVTVS     120
S                                                                    121

SEQ ID NO: 12            moltype = AA   length = 118
FEATURE                  Location/Qualifiers
source                   1..118
                         mol_type = protein
                         organism = synthetic construct
SEQUENCE: 12
QVQLVESGGG VVQPGRSLRL SCAASGFKFS GYGMHWVRQA PGKGLEWVAV IWFDGSRKYY      60
VDSVKGRFTI SRDNSKNTLY LQMNSLRAED TAVYYCARQM GYWHFGLWGR GTLVTVSS      118

SEQ ID NO: 13            moltype = AA   length = 107
FEATURE                  Location/Qualifiers
source                   1..107
                         mol_type = protein
                         organism = synthetic construct
SEQUENCE: 13
DIQMTQSPSS LSASVGDRVT ITCRASQGIN NSLTWYQQKP GKAPKLLIYG ASNRETGVPS      60
RFSGSGSGTD FTLTISSLQP EDFATYYCQQ WLKLPPTFGQ GTKVEIK                  107

SEQ ID NO: 14            moltype = AA   length = 107
FEATURE                  Location/Qualifiers
source                   1..107
                         mol_type = protein
                         organism = synthetic construct
SEQUENCE: 14
DIQMTQSPSS LSASVGDRVT ITCRASQSIS NYLTWYQQKP GKAPKLLIYE ASSRPSGVPS      60
RFSGSGSGTD FTLTISSLQP EDFATYYCQQ WSRLPVTFGQ GTKVEIK                  107

SEQ ID NO: 15            moltype = AA   length = 12
FEATURE                  Location/Qualifiers
source                   1..12
                         mol_type = protein
                         organism = synthetic construct
SEQUENCE: 15
ERKSCVECPP CP                                                         12

SEQ ID NO: 16            moltype = AA   length = 107
FEATURE                  Location/Qualifiers
source                   1..107
                         mol_type = protein
                         organism = synthetic construct
SEQUENCE: 16
DIQMTQSPSS LSASVGDRVT ITCSASQDIS NYLNWYQQKP GKAPKLLIYY TSNLHSGVPS      60
RFSGSGSGTD FTLTISSLQP EDFATYYCQQ YRKLPWTFGQ GTKLEIK                  107

SEQ ID NO: 17            moltype = AA   length = 330
FEATURE                  Location/Qualifiers
source                   1..330
                         mol_type = protein
                         organism = synthetic construct
SEQUENCE: 17
ASTKGPSVFP LAPSSKSTSG GTAALGCLVK DYFPEPVTVS WNSGALTSGV HTFPAVLQSS      60
GLYSLSSVVT VPSSSLGTQT YICNVNHKPS NTKVDKRVEP KSCDKTHTCP PCPAPELLGG     120
PSVFLFPPKP KDTLMISRTP EVTCVVVDVS HEDPEVKFNW YVDGVEVHNA KTKPREEQYN     180
STYRVVSVLT VLHQDWLNGK EYKCKVSNKA LPAPIEKTIS KAKGQPREPQ VYTLPPCREE     240
MTKNQVSLWC LVKGFYPSDI AVEWESNGQP ENNYKTTPPV LDSDGSFFLY SKLTVDKSRW     300
QQGNVFSCSV MHEALHNHYT QKSLSLSPGK                                     330

SEQ ID NO: 18            moltype = AA   length = 330
FEATURE                  Location/Qualifiers
source                   1..330
                         mol_type = protein
                         organism = synthetic construct
SEQUENCE: 18
ASTKGPSVFP LAPSSKSTSG GTAALGCLVK DYFPEPVTVS WNSGALTSGV HTFPAVLQSS      60
GLYSLSSVVT VPSSSLGTQT YICNVNHKPS NTKVDKRVEP KSCDKTHTCP PCPAPEFEGG     120
PSVFLFPPKP KDTLMISRTP EVTCVVVDVS HEDPEVKFNW YVDGVEVHNA KTKPREEQYN     180
STYRVVSVLT VLHQDWLNGK EYKCKVSNKA LPASIEKTIS KAKGQPREPQ VCTLPPSREE     240
MTKNQVSLSC AVKGFYPSDI AVEWESNGQP ENNYKTTPPV LDSDGSFFLV SKLTVDKSRW     300
QQGNVFSCSV MHEALHNHYT QKSLSLSPGK                                     330

SEQ ID NO: 19            moltype = AA   length = 330
```

-continued

```
FEATURE              Location/Qualifiers
source               1..330
                     mol_type = protein
                     organism = synthetic construct
SEQUENCE: 19
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKRVEP KSCDKTHTCP PCPAPEFEGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPASIEKTIS KAKGQPREPQ VYTLPPCREE  240
MTKNQVSLWC LVKGFYPSDI AVEWESNGQP ENNYKTTPPV LDSDGSFFLY SKLTVDKSRW  300
QQGNVFSCSV MHEALHNHYT QKSLSLSPGK                                   330

SEQ ID NO: 20        moltype = AA   length = 107
FEATURE              Location/Qualifiers
source               1..107
                     mol_type = protein
                     organism = Homo sapiens
SEQUENCE: 20
RTVAAPSVFI FPPSDEQLKS GTASVVCLLN NFYPREAKVQ WKVDNALQSG NSQESVTEQD   60
SKDSTYSLSS TLTLSKADYE KHKVYACEVT HQGLSSPVTK SFNRGEC                 107

SEQ ID NO: 21        moltype = AA   length = 106
FEATURE              Location/Qualifiers
source               1..106
                     mol_type = protein
                     organism = Homo sapiens
SEQUENCE: 21
GQPKAAPSVT LFPPSSEELQ ANKATLVCLI SDFYPGAVTV AWKADSSPVK AGVETTTPSK   60
QSNNKYAASS YLSLTPEQWK SHRSYSCQVT HEGSTVEKTV APTECS                 106

SEQ ID NO: 22        moltype = AA   length = 105
FEATURE              Location/Qualifiers
source               1..105
                     mol_type = protein
                     organism = Homo sapiens
SEQUENCE: 22
QDGNEEMGGI TQTPYKVSIS GTTVILTCPQ YPGSEILWQH NDKNIGGDED DKNIGSDEDH   60
LSLKEFSELE QSGYYVCYPR GSKPEDANFY LYLRARVCEN CMEMD                  105

SEQ ID NO: 23        moltype = AA   length = 84
FEATURE              Location/Qualifiers
source               1..84
                     mol_type = protein
                     organism = Homo sapiens
SEQUENCE: 23
FKIPIEELED RVFVNCNTSI TWVEGTVGTL LSDITRLDLG KRILDPRGIY RCNGTDIYKD   60
KESTVQVHYR MCQSCVELDP ATVA                                         84

SEQ ID NO: 24        moltype = AA   length = 96
FEATURE              Location/Qualifiers
source               1..96
                     mol_type = protein
                     organism = Macaca fascicularis
SEQUENCE: 24
QDGNEEMGSI TQTPYQVSIS GTTVILTCSQ HLGSEAQWQH NGKNKEDSGD RLFLPEFSEM   60
EQSGYYVCYP RGSNPEDASH HLYLKARVCE NCMEMD                            96

SEQ ID NO: 25        moltype = AA   length = 84
FEATURE              Location/Qualifiers
source               1..84
                     mol_type = protein
                     organism = Macaca fascicularis
SEQUENCE: 25
FKIPVEELED RVFVKCNTSV TWVEGTVGTL LTNNTRLDLG KRILDPRGIY RCNGTDIYKD   60
KESAVQVHYR MCQNCVELDP ATLA                                         84

SEQ ID NO: 26        moltype = AA   length = 87
FEATURE              Location/Qualifiers
source               1..87
                     mol_type = protein
                     organism = Mus musculus
SEQUENCE: 26
DDAENIEYKV SISGTSVELT CPLDSDENLK WEKNGQELPQ KHDKHLVLQD FSEVEDSGYY   60
VCYTPASNKN TYLYLKARVC EYCVEVD                                      87

SEQ ID NO: 27        moltype = AA   length = 84
FEATURE              Location/Qualifiers
source               1..84
                     mol_type = protein
```

-continued

```
                              organism = Mus musculus
SEQUENCE: 27
FKIQVTEYED KVFVTCNTSV MHLDGTVEGW FAKNKTLNLG KGVLDPRGIY LCNGTEQLAK   60
VVSSVQVHYR MCQNCVELDS GTMA                                          84

SEQ ID NO: 28            moltype = AA   length = 54
FEATURE                  Location/Qualifiers
source                   1..54
                         mol_type = protein
                         organism = Homo sapiens
SEQUENCE: 28
MLQMAGQCSQ NEYFDSLLHA CIPCQLRCSS NTPPLTCQRY CNASVTNSVK GTNA         54

SEQ ID NO: 29            moltype = AA   length = 52
FEATURE                  Location/Qualifiers
source                   1..52
                         mol_type = protein
                         organism = Macaca fascicularis
SEQUENCE: 29
MLQMARQCSQ NEYFDSLLHD CKPCQLRCSS TPPLTCQRYC NASMTNSVKG MN           52

SEQ ID NO: 30            moltype = AA   length = 49
FEATURE                  Location/Qualifiers
source                   1..49
                         mol_type = protein
                         organism = Mus musculus
SEQUENCE: 30
MAQQCFHSEY FDSLLHACKP CHLRCSNPPA TCQPYCDPSV TSSVKGTYT              49

SEQ ID NO: 31            moltype = AA   length = 6
FEATURE                  Location/Qualifiers
source                   1..6
                         mol_type = protein
                         organism = synthetic construct
SEQUENCE: 31
HHHHHH                                                              6

SEQ ID NO: 32            moltype = AA   length = 232
FEATURE                  Location/Qualifiers
source                   1..232
                         mol_type = protein
                         organism = Mus musculus
SEQUENCE: 32
PRGPTIKPCP PCKCPAPNLL GGPSVFIFPP KIKDVLMISL SPIVTCVVVD VSEDDPDVQI   60
SWFVNNVEVH TAQTQTHRED YNSTLRVVSA LPIQHQDWMS GKEFKCKVNN KDLPAPIERT   120
ISKPKGSVRA PQVYVLPPPE EEMTKKQVTL TCMVTDFMPE DIYVEWTNNG KTELNYKNTE   180
PVLDSDGSYF MYSKLRVEKK NWVERNSYSC SVVHEGLHNH HTTKSFSRTP GK           232

SEQ ID NO: 33            moltype = AA   length = 232
FEATURE                  Location/Qualifiers
source                   1..232
                         mol_type = protein
                         organism = synthetic construct
SEQUENCE: 33
EPKSSDKTHT CPPCPAPELL GGPSVFLFPP KPKDTLMISR TPEVTCVVVD VSHEDPEVKF   60
NWYVDGVEVH NAKTKPREEQ YNSTYRVVSV LTVLHQDWLN GKEYKCKVSN KALPAPIEKT   120
ISKAKGQPRE PQVYTLPPCR EEMTKNQVSL WCLVKGFYPS DIAVEWESNG QPENNYKTTP   180
PVLDSDGSFF LYSKLTVDKS RWQQGNVFSC SVMHEALHNH YTQKSLSLSP GK           232

SEQ ID NO: 34            moltype = AA   length = 232
FEATURE                  Location/Qualifiers
source                   1..232
                         mol_type = protein
                         organism = synthetic construct
SEQUENCE: 34
EPKSSDKTHT CPPCPAPELL GGPSVFLFPP KPKDTLMISR TPEVTCVVVD VSHEDPEVKF   60
NWYVDGVEVH NAKTKPREEQ YNSTYRVVSV LTVLHQDWLN GKEYKCKVSN KALPAPIEKT   120
ISKAKGQPRE PQVCTLPPSR EEMTKNQVSL SCAVKGFYPS DIAVEWESNG QPENNYKTTP   180
PVLDSDGSFF LVSKLTVDKS RWQQGNVFSC SVMHEALHNH YTQKSLSLSP GK           232

SEQ ID NO: 35            moltype = AA   length = 330
FEATURE                  Location/Qualifiers
source                   1..330
                         mol_type = protein
                         organism = Homo sapiens
SEQUENCE: 35
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKRVEP KSCDKTHTCP PCPAPELLGG   120
PSVFLFPPKP KDTLMISRTP EVTCVVVDVS HEDPEVKFNW YVDGVEVHNA KTKPREEQYN   180
```

```
STYRVVSVLT VLHQDWLNGK EYKCKVSNKA LPAPIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                   330

SEQ ID NO: 36            moltype = AA   length = 330
FEATURE                  Location/Qualifiers
source                   1..330
                         mol_type = protein
                         organism = synthetic construct
SEQUENCE: 36
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKRVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VCTLPPSREE  240
MTKNQVSLSC AVKGFYPSDI AVEWESNGQP ENNYKTTPPV LDSDGSFFLV SKLTVDKSRW  300
QQGNVFSCSV MHEALHNHYT QKSLSLSPGK                                   330

SEQ ID NO: 37            moltype = AA   length = 327
FEATURE                  Location/Qualifiers
source                   1..327
                         mol_type = protein
                         organism = synthetic construct
SEQUENCE: 37
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKRVER KSCVECPPCP APEFEGGPSV  120
FLFPPKPKDT LMISRTPEVT CVVVDVSHED PEVKFNWYVD GVEVHNAKTK PREEQYNSTY  180
RVVSVLTVLH QDWLNGKEYK CKVSNKALPA SIEKTISKAK GQPREPQVYT LPPCREEMTK  240
NQVSLWCLVK GFYPSDIAVE WESNGQPENN YKTTPPVLDS DGSFFLYSKL TVDKSRWQQG  300
NVFSCSVMHE ALHNHYTQKS LSLSPGK                                     327

SEQ ID NO: 38            moltype = AA   length = 327
FEATURE                  Location/Qualifiers
source                   1..327
                         mol_type = protein
                         organism = synthetic construct
SEQUENCE: 38
ASTKGPSVFP LAPSSKSTSE GTAALGCLVK DYFPEPVTVS WNSGALTSGV HTFPAVLQSS  60
GLYSLSSVVT VPSSSLGTQT YICNVDHKPS NTKVDKTVER KSCVECPPCP APEFEGGPSV  120
FLFPPKPKDT LMISRTPEVT CVVVDVSQED PEVQFNWYVD GVEVHNAKTK PREEQYNSTY  180
RVVSVLTVLH QDWLNGKEYK CKVSNKALPA SIEKTISKAK GQPREPQVCT LPPSQEEMTK  240
NQVSLSCAVK GFYPSDIAVE WESNGQPENN YKTTPPVLDS DGSFFLVSKL TVDKSRWQEG  300
NVFSCSVMHE ALHNHYTQKS LSLSPGK                                     327

SEQ ID NO: 39            moltype = AA   length = 445
FEATURE                  Location/Qualifiers
source                   1..445
                         mol_type = protein
                         organism = synthetic construct
SEQUENCE: 39
QVQLVESGGG VVQPGRSLRL SCAASGFKFS GYGMHWVRQA PGKGLEWVAV IWFDGSRKYY  60
VDSVKGRFTI SRDNSKNTLY LQMNSLRAED TAVYYCARQM GYWHFGLWGR GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKRVERKS CVECPPCPAP EFEGGPSVFL  240
FPPKPKDTLM ISRTPEVTCV VVDVSHEDPE VKFNWYVDGV EVHNAKTKPR EEQYNSTYRV  300
VSVLTVLHQD WLNGKEYKCK VSNKALPASI EKTISKAKGQ PREPQVYTLP PCREEMTKNQ  360
VSLWCLVKGF YPSDIAVEWE SNGQPENNYK TTPPVLDSDG SFFLYSKLTV DKSRWQQGNV  420
FSCSVMHEAL HNHYTQKSLS LSPGK                                      445

SEQ ID NO: 40            moltype = AA   length = 448
FEATURE                  Location/Qualifiers
source                   1..448
                         mol_type = protein
                         organism = synthetic construct
SEQUENCE: 40
QVQLVQSGAE VKKPGSSVKV SCKASGYTFT NYWMHWVRQA PGQGLEWMGA TYRGHSDTYY  60
NQKFKGRVTI TADKSTSTAY MELSSLRSED TAVYYCTRGA VYAGYDVLDY WGQGTTVTVS  120
SASTKGPSVF PLAPSSKSTS EGTAALGCLV KDYFPEPVTV SWNSGALTSG VHTFPAVLQS  180
SGLYSLSSVV TVPSSSLGTQ TYICNVDHKP SNTKVDKTVE RKSCVECPPC APEFEGGPS  240
VFLFPPKPKD TLMISRTPEV TCVVVDVSQE DPEVQFNWYV DGVEVHNAKT KPREEQYNST  300
YRVVSVLTVL HQDWLNGKEY KCKVSNKALP ASIEKTISKA KGQPREPQVC TLPPSQEEMT  360
KNQVSLSCAV KGFYPSDIAV EWESNGQPEN NYKTTPPVLD SDGSFFLVSK LTVDKSRWQE  420
GNVFSCSVMH EALHNHYTQK SLSLSPGK                                    448

SEQ ID NO: 41            moltype = AA   length = 214
FEATURE                  Location/Qualifiers
source                   1..214
                         mol_type = protein
                         organism = synthetic construct
SEQUENCE: 41
```

```
DIQMTQSPSS LSASVGDRVT ITCRASQSIS NYLTWYQQKP GKAPKLLIYE ASSRPSGVPS    60
RFSGSGSGTD FTLTISSLQP EDFATYYCQQ WSRLPVTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 42            moltype = AA  length = 448
FEATURE                  Location/Qualifiers
source                   1..448
                         mol_type = protein
                         organism = synthetic construct
SEQUENCE: 42
QVQLVESGGG VVQPGRSLRL SCAASGFKFS GYGMHWVRQA PGKGLEWVAV IWFDGSRKYY    60
VDSVKGRFTI SRDNSKNTLY LQMNSLRAED TAVYYCARQM GYWHFGLWGR GTLVTVSSAS   120
TKGPSVFPLA PSSKSTSGGT AALGCLVKDY FPEPVTVSWN SGALTSGVHT FPAVLQSSGL   180
YSLSSVVTVP SSSLGTQTYI CNVNHKPSNT KVDKRVEPKS CDKTHTCPPC PAPEFEGGPS   240
VFLFPPKPKD TLMISRTPEV TCVVVDVSHE DPEVKFNWYV DGVEVHNAKT KPREEQYNST   300
YRVVSVLTVL HQDWLNGKEY KCKVSNKALP ASIEKTISKA KGQPREPQVY TLPPCREEMT   360
KNQVSLWCLV KGFYPSDIAV EWESNGQPEN NYKTTPPVLD SDGSFFLYSK LTVDKSRWQQ   420
GNVFSCSVMH EALHNHYTQK SLSLSPGK                                     448

SEQ ID NO: 43            moltype = AA  length = 451
FEATURE                  Location/Qualifiers
source                   1..451
                         mol_type = protein
                         organism = synthetic construct
SEQUENCE: 43
QVQLVQSGAE VKKPGSSVKV SCKASGYTFT NYWMHWVRQA PGQGLEWMGA TYRGHSDTYY    60
NQKFKGRVTI TADKSTSTAY MELSSLRSED TAVYYCTRGA VYAGYDVLDY WGQGTTVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKRVE PKSCDKTHTC PPCPAPEFEG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPASIEKTI SKAKGQPREP QVCTLPPSRE   360
EMTKNQVSLS CAVKGFYPSD IAVEWESNGQ PENNYKTTPP VLDSDGSFFL VSKLTVDKSR   420
WQQGNVFSCS VMHEALHNHY TQKSLSLSPG K                                 451
```

BCMA × CD3 T BISPECIFIC CELL ENGAGER

CROSS-REFERENCE TO RELATED APPLICATIONS

The present application claims priority to U.S. Provisional patent application 63/824,363, filed on Jun. 16, 2025, and international patent application PCT/CN2025/098722, filed on Jun. 3, 2025, each of which is hereby incorporated by reference in its entirety.

INCORPORATION BY REFERENCE OF AN ELECTRONIC SEQUENCE LISTING

This application contains a sequence listing that has been submitted in a computer readable format and is hereby incorporated by reference in its entirety. The computer readable file, created on Jun. 1, 2025, is named GR1803_COM_PCT.xml and is 44,103 bytes in size.

BACKGROUND

Bispecific antibodies (BsAbs) represent a well-established platform in drug development for cancer. One of the most common classes of BsAbs are bispecific T-cell engagers (TCE), which function by simultaneously engaging target associated antigens (TAAs) on the one hand and an immune-related molecule (e.g., CD3) on the other. These molecules engage T cells through T-cell activation independent of MHC expression or recognition of cognate antigen. This interaction results in the release of cytotoxic molecules, such as perforins and granzymes, and the induction of cytokines. Additionally, BsAbs can be harnessed to modulate immune responses by co-engaging inhibitory receptors, such as PD-L1/CTLA-4, or immune-stimulatory receptors, including the TNF receptors OX40, CD27, CD137 (4-1BB), or the T-cell costimulatory receptor CD28. Targeting these pathways and/or receptors may enhance antitumor immune response or activate exhausted tumor-infiltrating lymphocytes within the tumor immune microenvironment.

There are numerous platforms for bispecific antibodies and their structures are complex. In terms of antibody structures, bispecific antibodies can be divided into two categories: those with Fc segments and those without Fc segments. The bispecific antibodies without Fc segments consist of the VH and VL regions or Fab fragments from two antibodies. Some of the BsAbs that have been approved for the treatment of various malignancies include amivantamab (EGFR/cMET), blinatumomab (CD3/CD19), catumaxomab (CD3/EpCAM), mosunetuzumab (CD3/CD20), tebentafusp (GP100/CD3), teclistamab (CD3/BCMA), and ze-nocutuzumab (HER2/HER3).

The advantage of such bispecific antibodies is that there is no mismatch between heavy and light chains, and the disadvantage is that the half-life is short and the clinical application is inconvenient. The bispecific antibodies with Fc segments retain the structures of conventional monoclonal antibodies and can mediate the biological function of the Fc segments. The representatives of such bispecific antibodies are KIH IgG, crossmab, DVD-Ig, Triomab, and the like, which have a long half-life in vivo and can have ADCC and CDC activities (Hongyan Liu, Abhishek Saxena, Sachdev S. Sidhu, et al., Fc engineering for Developing Therapeutic Bispecifc Antibodies and Novel Scaffolds. *Front. Immunol.* 2017; 8:38).

BRIEF SUMMARY

Described herein, in certain embodiments, a bispecific antibody described herein.

On aspect of the disclosure relates to a bispecific antibody comprising a first arm and a second arm, wherein the first arm comprises the amino acid sequences of SEQ ID NOs: 39 and 41 and the second arm comprises the amino acid sequences of SEQ ID NOs: 40 and 41.

One aspect of the disclosure relates to a bispecific antibody comprising a first arm and a second arm, wherein the first arm comprises a first antigen-binding portion against human CD3E, wherein the first arm comprises a heavy chain variable region comprising an amino acid sequence at least 80% identical to the amino acid sequence of SEQ ID NO:12, a heavy chain constant region comprising an amino acid sequence at least 80% identical to the amino acid sequence of SEQ ID NO:37, a light chain variable region comprising an amino acid sequence at least 80% identical to the amino acid sequence of SEQ ID NO: 14, and a light chain constant region comprising an amino acid sequence at least 80% identical to the amino acid sequence of SEQ ID NO: 20, and and the second arm comprises a second antigen-binding portion against human BCMA, wherein the second arm comprises a heavy chain variable region comprising an amino acid sequence at least 80% identical to the amino acid sequence of SEQ ID NO:10, a heavy chain constant region comprising an amino acid sequence at least 80% identical to the amino acid sequence of SEQ ID NO:38, a light chain variable region comprising an amino acid sequence at least 80% identical to the amino acid sequence of SEQ ID NO:14, and a light chain constant region an amino acid sequence at least 80% identical to the amino acid sequence of SEQ ID NO:20.

One aspect of the disclosure relates to a pharmaceutical composition including any one of the disclosed bispecific antibodies and a pharmaceutically acceptable carrier or excipient.

In an aspect, the first arm comprises a heavy chain variable region comprising an amino acid sequence at least 85% identical, alternatively at least 88% identical, alternatively at least 90% identical, alternatively at least 91% identical, alternatively at least 92% identical, alternatively at least 93% identical, alternatively at least 94% identical, alternatively at least 95% identical, alternatively at least 96% identical, alternatively at least 97% identical, alternatively at least 98% identical, or alternatively at least 99% identical to the amino acid sequence of SEQ ID NO:12.

In an aspect, the first arm comprises a heavy chain variable region comprising the amino acid sequence of SEQ ID NO:12.

In an aspect, the first arm comprises a heavy chain constant region comprising an amino acid sequence at least 85% identical, alternatively at least 88% identical, alternatively at least 90% identical, alternatively at least 91% identical, alternatively at least 92% identical, alternatively at least 93% identical, alternatively at least 94% identical, alternatively at least 95% identical, alternatively at least 96% identical, alternatively at least 97% identical, alternatively at least 98% identical, or alternatively at least 99% identical to the amino acid sequence of SEQ ID NO:37.

In an aspect, the first arm comprises a heavy chain constant region comprising the amino acid sequence of SEQ ID NO:37.

In an aspect, the second arm comprises a heavy chain variable region comprising an amino acid sequence at least 85% identical, alternatively at least 88% identical, alternatively at least 90% identical, alternatively at least 91% identical, alternatively at least 92% identical, alternatively at least 93% identical, alternatively at least 94% identical, alternatively at least 95% identical, alternatively at least 96% identical, alternatively at least 97% identical, alternatively at least 98% identical, or alternatively at least 99% identical to the amino acid sequence of SEQ ID NO:10.

In an aspect, the second arm comprises a heavy chain variable region comprising the amino acid sequence of SEQ ID NO:10.

In an aspect, the second arm comprises a heavy chain constant region comprising an amino acid sequence at least 85% identical, alternatively at least 88% identical, alternatively at least 90% identical, alternatively at least 91% identical, alternatively at least 92% identical, alternatively at least 93% identical, alternatively at least 94% identical, alternatively at least 95% identical, alternatively at least 96% identical, alternatively at least 97% identical, alternatively at least 98% identical, or alternatively at least 99% identical to the amino acid sequence of SEQ ID NO:38.

In an aspect, the second arm comprises a heavy chain constant region comprising the amino acid sequence of SEQ ID NO:38.

In an aspect, the first arm and/or the second arm comprises a light chain variable region comprising an amino acid sequence at least 85% identical, alternatively at least 88% identical, alternatively at least 90% identical, alternatively at least 91% identical, alternatively at least 92% identical, alternatively at least 93% identical, alternatively at least 94% identical, alternatively at least 95% identical, alternatively at least 96% identical, alternatively at least 97% identical, alternatively at least 98% identical, or alternatively at least 99% identical to the amino acid sequence of SEQ ID NO: 14.

In an aspect, the first arm and/or the second arm comprises a light chain variable region comprising the amino acid sequence of SEQ ID NO: 14.

In an aspect, the first arm and/or the second arm comprises a light chain constant region comprising an amino acid sequence at least 85% identical, alternatively at least 88% identical, alternatively at least 90% identical, alternatively at least 91% identical, alternatively at least 92% identical, alternatively at least 93% identical, alternatively at least 94% identical, alternatively at least 95% identical, alternatively at least 96% identical, alternatively at least 97% identical, alternatively at least 98% identical, or alternatively at least 99% identical to the amino acid sequence of SEQ ID NO:20.

In an aspect, the first arm and/or the second arm comprises a light chain constant region comprising the amino acid sequence of SEQ ID NO:20.

In an aspect, the bispecific antibody is an IgG1 antibody comprising two heavy chain constant regions having the same hinge region, wherein the amino acid sequence of the hinge region is at least about 80% identical to the amino acid sequence of SEQ ID NO:15.

In an aspect, the hinge region comprises the amino acid sequence of SEQ ID NO: 15.

In an aspect, the first antigen-binding portion comprises a single chain antibody (scfv) or a Fab fragment.

In an aspect, the second antigen-binding portion comprises a single chain antibody (scfv) or a Fab fragment.

In an aspect, the first antigen-binding portion comprises a Fab fragment and the second antigen-binding portion comprises a Fab fragment; or the first antigen-binding portion comprises a Fab fragment, and the second antigen-binding portion comprises a single chain antibody (scfv); or the first antigen-binding portion comprises a single chain antibody (scfv), and the second antigen-binding portion comprises a Fab fragment; or the first antigen-binding portion comprises a single chain antibody (scfv), and the second antigen-binding portion comprises a single chain antibody (scfv).

In an aspect, the bispecific antibody has an isoelectric point between about 8.5 to about 9.5, alternatively about 9.0.

In an aspect, the HC (anti-BCMA) $N_{298}$/HC (anti-CD3) $N_{295}$ comprises at least one glycosylation modification.

In an aspect, the main glycoform is A2G0F.

In an aspect, the proportion of A2G0F glycoform is between about 73.0% and about 73.5%.

In an aspect, the affinity constant KD to CD3D & CD3E antigen is between about $1.261 \times 10^{-7}$M and about $2.412 \times 10^{-7}$M.

In an aspect, the affinity constant KD to BCMA-his antigen is between about $4.880 \times 10^{-10}$ M and about $5.405 \times 10^{-10}$ M.

In an aspect, the bispecific antibody can bind to FcRn under acidic conditions, the affinity constant KD is between about $7.917 \times 10^{-5}$ M and $9.243 \times 10^{-5}$ M, and the $EC_{50}$ value is between about 2.405 μg/ml and about 2.455 μg/ml.

v the bispecific antibody has an affinity constant KD was $9.243 \times 10^{-5}$ M and a $EC_{50}$ value of 2.405 μg/ml.

In an aspect, the bispecific antibody has affinity constant KD of $7.917 \times 10^{-5}$ M and a $EC_{50}$ value of 2.455 μg/ml.

v the bispecific antibody can bind to CD3D & CD3E and BCMA-his antigen simultaneously and the binding activity $EC_{50}$ is between about 3.224 μg/ml and about 8.183 μg/ml.

In an aspect, the bispecific antibody can engage T cells with BCMA positive tumor cells in vitro and activate T cells and the binding activity $EC_{50}$ is between about 0.045 μg/ml and about 0.049 μg/ml.

In an aspect, the bispecific antibody has a melting temperature of about 61° C.

In an aspect, the bispecific antibody has good thermal stability.

In an aspect, the deamidation modification the bispecific antibody occurs at:

HC (anti-BCMA) $N_{316}$/HC (anti-CD3) $N_{313}$ at a proportion of 2.2%-2.3%,

HC (anti-BCMA) $N_{362}$ at a proportion of 1.2%, $N_{385}$ at a proportion of 1.5%, HC (anti-BCMA) $N_{390}$/HC (anti-CD3) $N_{387}$ at a proportion of 6.1-6.2%, and/or HC (anti-BCMA) $N_{435}$/HC (anti-CD3) $N_{437}$ at a proportion of 2.6-2.7%.

In an aspect, the oxidative modification occurs at:

LC $M_4$ at a proportion of 0.1%,

HC (anti-BCMA) $M_{34}$ at a proportion of 0.5%-0.6%, $_{162}$ of heavy chain at a proportion of 0.3%, HC (anti-BCMA) $M_{253}$/HC (anti-CD3) $M_{250}$ at a proportion of 4.2%-5.1%, HC (anti-BCMA) $M_{429}$ at a proportion of 0.8%-0.9%, HC (anti-CD3) $M_{100}$ at a proportion of 9.5%-11.4%, and/or HC (anti-CD3) $M_{426}$ at a proportion of 0.3%.

In an aspect, the bispecific antibody can T cells by specifically binding to CD3 on the surface of T cells and BCMA on the surface of tumor cells.

These and other advantages, aspects, and novel features of the present disclosure, as well as details of illustrated embodiments thereof, will be more fully understood from the following description and drawings.

BRIEF DESCRIPTION OF THE DRAWINGS

Various aspects of the present disclosure will now be described, by way of example only, with reference to the attached Figures, wherein.

DETAILED DESCRIPTION

I. Introduction

Bispecific antibodies, such as bispecific T cell engaging (TCE) antibodies targeting B cell surface antigens provide an alternative means of delivering T cell redirecting therapy that has shown similar potential to induce deep depletion of both normal and malignant B cells in patients with B cell acute lymphoblastic leukemia and non-Hodgkin lymphoma (Tian, 2021). Deep and durable responses in patients with various B cell malignancies suggest that the TCE approach can induce similarly potent depletion of tissue-resident B cell populations. SLE is a classic B-cell-mediated autoimmune disease, while rheumatoid arthritis and type 1 diabetes were initially considered to be predominantly T-cell mediated. However, recent studies suggest a role of B cells in the pathogenesis of these autoimmune diseases.

Figures 1, 2:
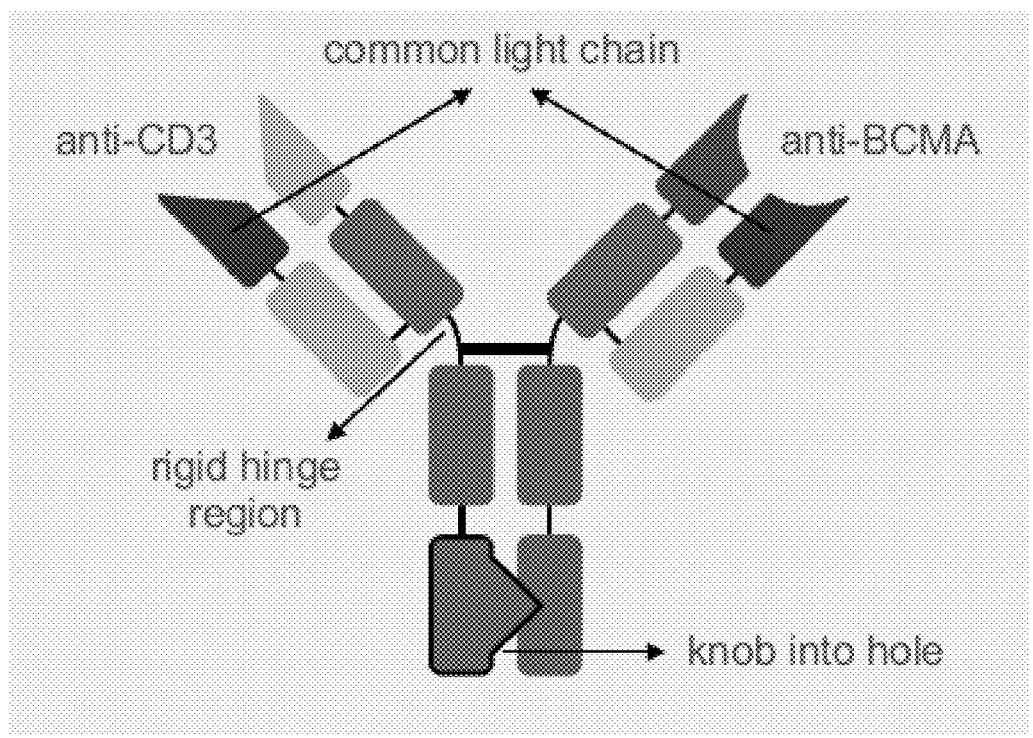
FIG. 1 shows the structure of GR1803 (also known as Velinotamig).
FIG. 2 shows the results of detecting the simultaneous binding of the bispecific antibody CD3ExBCMA to both CD3E and BCMA antigens by using the ELISA method.

Provided in the present application a bispecific antibody comprising a first antigen-binding portion against human CD3E and a second antigen-binding portion against human BCMA. An exemplary bispecific antibody, GR1803 (also known as Velinotamig), is shown in FIG. 1. GR1803 binds to the BCMA and CD3 antigens, redirecting cytotoxic T cells to target BCMA-expressing cells. The bispecific antibody also has a high affinity for BCMA and lower affinity for CD3. The affinity for BCMA is two orders of magnitude higher than for CD3, promoting recruitment and activation of T cells while minimizing non-specific T cell activation. GR1803 eliminates BCMA+ plasma cells by using rigid hinge region to enhance synapse formation between T cell and target cells and has a similar structure as classic monoclonal antibody and possible lower immunogenicity by using common light chain.

Before continuing to describe the present disclosure in further detail, it will be understood that the materials, methods, and examples are illustrative only and not intended to be limiting. Methods and materials are described herein for use in the present invention and other, suitable methods and materials known in the art can also be used. All publications, patent applications, patents, sequences, database entries, and other references mentioned herein are incorporated by reference in their entirety. In case of conflict, the present specification, including definitions, will control.

II. Definitions

The following definitions and methods are provided to better define the present application and guide those of ordinary skill in the art in the practice of the present application. Unless otherwise indicated, the terms used in the present application have the meanings commonly understood by those skilled in the art. All patent documents, academic papers, and other publications cited herein are incorporated by reference in their entirety.

When describing the structure of the antibody herein, reference is made to the EU numbering definition of human IgG1 antibody with respect to the description on amino acid position numbering, which is well known and readily available to those skilled in the art. Furthermore, where a mutation is described herein in connection with the EU numbering position, it refers to a mutation produced relative to the native antibody sequence.

As used herein, the term "Fc fragment", "Fc domain", "Fc portion" or the like refers to a portion of the heavy chain constant region of an antibody, including the hinge region, the CH2 segment and the CH3 segment of the constant region. With reference to the EU numbering definition of the human IgG1 antibody, the Fc fragment refers to the amino acid sequence at positions 216-447 in the constant region of the antibody.

As used herein, the term "Fab (fragment antigen-binding) fragment", "Fab portion", or the like refers to an antibody fragment capable of binding to an antigen that are produced after treatment of an intact antibody with papain, including the intact light chain (VL-CL), the heavy chain variable region, and the CHI fragment (VH-CH1).

As used herein, the term "single chain fragment variable (scFv)" refers to an antibody of a single chain structure comprising a polypeptide chain comprising a heavy chain variable region (VH) and a light chain variable region (VL), which is generally constructed using genetic engineering techniques. A flexible linker is typically designed between the heavy chain variable region and the light chain variable region so that the heavy chain variable region and the light chain variable region can be folded into the correct conformation capable of binding to an antigen.

As used herein, the term "antigen-binding portion" refers to a portion of the antibody structure that determines the antigen-binding ability. It will be appreciated by those skilled in the art that the major parts of the antibody structure that determines the antigen-binding ability are the CDRs, so the CDRs are also the core components of the antigen-binding portion. In the construction of a bispecific antibody, the examples of the "antigen-binding portion" include, but are not limited to, a single chain antibody (scfv) or a Fab fragment.

As used herein, the term "bispecific antibody" refers to an antibody having the ability to bind to two different antigens, which may consist of two Fc fragments and two antigen-binding portions fused thereto, respectively.

In some embodiments, "bispecific antibody" used herein refers to a bispecific antibody based on human IgG1 antibody, and in addition to the altered structures described herein, it has the basic characteristics and function of human IgG1 antibody. It is well-known to those skilled in the art that "bispecific antibody" used herein may also be a bispecific antibody based on other immunoglobulin subtype, such as human IgG2 antibody.

It is well known to those skilled in the art that complementarity determining regions (CDRs, usually including CDR1, CDR2 and CDR3) are the regions of a variable region that have mostly impact on the affinity and specificity of an antibody. The CDR sequences of a VH or VL have two common definitions, i.e., the Kabat definition and the Chothia definition (see, e.g., Kabat, "Sequences of Proteins of Immunological Interest", National Institutes of Health, Bethesda, Md. (1991); Al-Lazikani et al., *J. Mol. Biol.* 273:927-948 (1997); and Martin et al., *Proc. Natl. Acad. Sci. USA,* 86:9268-9272 (1989)). For the variable region sequences of a given antibody, the sequences of CDR regions in the VH and VL can be determined according to the Kabat definition or the Chothia definition. In some embodiments of the present application, CDR sequences are defined according to the Kabat definition.

For the variable region sequences of a given antibody, the sequences of CDR regions in the variable region sequences can be analyzed in a variety of ways, for example, using online software Abysis (abysis.org).

As used herein, the term "specific binding" refers to a non-random binding reaction between two molecules, e.g., binding of an antibody to an antigen epitope.

Multiple myeloma is a B cell malignant tumor caused by malignant proliferation and canceration of cells. It is mainly manifested by the uncontrolled expansion of plasma cells in the bone man ow and the production of a large number of monoclonal immunoglobulins, which result in a series of symptoms such as bone destruction, elevated blood calcium, anemia, renal damage, immune decline, and the like. The expression level of BCMA in myeloma cells is significantly higher than that in plasma cells and plasmablasts. BCMA is highly and widely expressed throughout the course of plasma cell malignant diseases including monoclonal gammopathy to smoldering myeloma, and further to multiple myeloma (Shih-Feng Cho, Kenneth C. Anderson, Yu-Tzu Tai. Targeting B Cell Maturation Antigen (BCMA) in Multiple Myeloma: Potential Uses of BCMA-Based immunotherapy. *Front. Immunol.,* 2018; 9:1821).

The singular form "a", "an" and "the" include plural referents unless the context clearly dictates otherwise. These articles refer to one or to more than one (i.e., to at least one). The term "and/or" means any one or more of the items in the list joined by "and/or". As an example, "x and/or y" means any element of the three-element set {(x), (y), (x, y)}. In other words, "x and/or y" means "one or both of x and y". As another example, "x, y, and/or z" means any element of the seven-element set {(x), (y), (z), (x, y), (x, z), (y, z), (x, y, z)}. In other words, "x, y and/or z" means "one or more of x, y and z".

The term "about" as used in connection with a numerical value throughout the specification and the claims denotes an interval of accuracy, familiar and acceptable to a person skilled in the art. In general, such interval of accuracy is +/−10%.

Where ranges are given, endpoints are included. Furthermore, unless otherwise indicated or otherwise evident from the context and understanding of one of ordinary skill in the art, values that are expressed as ranges can assume any specific value or subrange within the stated ranges in different embodiments of the disclosure, to the tenth of the unit of the lower limit of the range, unless the context clearly dictates otherwise.

The term "exemplary" means serving as a non-limiting example, instance, or illustration. As utilized herein, the terms "e.g.," and "for example" set off lists of one or more non-limiting aspects, examples, instances, or illustrations.

As used herein, the terms "subject", "individual", and "patient" are interchangeable, and relate to vertebrates, preferably mammals. For example, mammals in the context of the disclosure are humans, non-human primates, domesticated animals such as dogs, cats, sheep, cattle, goats, pigs, horses, etc., laboratory animals such as mice, rats, rabbits, guinea pigs, etc., as well as animals in captivity such as animals in zoos. The term "animal" as used herein includes humans. The term "subject" may also include a patient, i.e., an animal, having a disease. In exemplary aspects, a subject, individual, or patient refers to a human (e.g., a man, a woman, or a child).

The terms "treat", "treating", or "treatment" refer to administering to a subject a compound or pharmaceutical composition disclosed herein to partially or completely alleviate, inhibit, ameliorate, or relieve the disease or disorder from which the subject is suffering. This means any manner in which one or more of the symptoms of a disease or disorder are ameliorated or otherwise beneficially altered. As used herein, amelioration of the symptoms of a particular disease or disorder refers to any lessening, whether permanent or temporary, lasting or transient, that can be attributed to or associated with treatment by the compounds, compositions, and methods of the present disclosure. For example, treating a subject can mean eliminating or reducing the clinical signs of a disease or disorder in the subject; arrest, inhibit, or slow the progression of the disease or disorder in the subject; and/or decrease the number, frequency, or severity of clinical symptoms and/or recurrence of the disease or disorder in the subject who currently has or who previously had the disease or disorder. In particular, the terms "treatment of a disease" and "treating a disease" include curing, shortening in duration, ameliorating, slowing down, inhibiting progression or worsening, or delaying the onset of clinical symptoms in a subject who has the disease or disorder.

As used herein, the term "administering" as used herein refers to the physical introduction of an agent to a subject, using any of the various methods and delivery systems known to those skilled in the art. Exemplary routes of administration for the formulations disclosed herein include intravenous, intramuscular, subcutaneous, intraperitoneal, spinal, or other parenteral routes of administration, for example by injection or infusion. The phrase "parenteral administration" means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. In some embodiments, the formulation is administered via a non-parenteral route, e.g., orally. Other non-parenteral routes include a topical, epidermal or mucosal route of administration, for example, intranasally, vaginally, rectally, sublingually or topically. Administering can also be performed, for example, once, a plurality of times, and/or over one or more extended periods.

As used herein, an "effective amount", "effective dose", or "effective dosage" of a bispecific antibody described herein refers to an amount sufficient to elicit the desired biological response. An effective amount of a therapeutic agent described herein may vary depending on such factors as the desired biological endpoint, the pharmacokinetics of a therapeutic agent, the condition being treated, the mode of administration, and the age and health of the subject. In certain embodiments, an effective amount is a therapeutically effective amount. In certain embodiments, an effective amount is a prophylactic treatment. In certain embodiments, an effective amount is the amount of a compound described herein in a single dose. In certain embodiments, an effective amount is the combined amounts of a bispecific antibody described herein in multiple doses. Effective amount is also meant to encompass an amount sufficient to cure or at least partially arrest the disease and its complications in a patient already suffering from the disease.

In some aspects, the effective amount is a pharmaceutically effective amount or a therapeutic effective amount. The term "pharmaceutically acceptable" or "therapeutically effective" refers to a molecule or composition that, when administered to a recipient, is not deleterious to the recipient thereof, or that any deleterious effect is outweighed by a benefit to the recipient thereof. With respect to a carrier, diluent, or excipient used to formulate a composition as disclosed herein, a pharmaceutically acceptable or therapeutically acceptable carrier, diluent, or excipient must be compatible with the other ingredients of the composition and not deleterious to the recipient thereof, or any deleterious effect must be outweighed by a benefit to the recipient.

The term "pharmaceutically acceptable carrier" or "therapeutically effective carrier" means a pharmaceutically or therapeutically acceptable material, composition or vehicle, such as a liquid or solid filler, diluent, excipient, or solvent encapsulating material, involved in carrying or transporting an agent from one portion of the body to another (e.g., from one organ to another). Each carrier present in a must be "acceptable" in the sense of being compatible with the other ingredients of the formulation and not deleterious to the patient, or any deleterious effect must be outweighed by a benefit to the recipient. Some examples of materials which may serve as pharmaceutically acceptable carriers comprise: sugars, such as lactose, glucose and sucrose; starches, such as com starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, com oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogenfree water; isotonic saline; Ringer's solution; ethyl alcohol; pH buffered solutions; polyesters, polycarbonates and/or polyanhydrides; and other non-toxic compatible substances employed in pharmaceutical or therapeutic formulations.

The presently described technology and its advantages will be better understood by reference to the following examples. These examples are provided to describe specific implementations of the present technology. By providing these specific examples, it is not intended limit the scope and spirit of the present technology. It will be understood by those skilled in the art that the full scope of the presently described technology encompasses the subject matter defined by the claims appending this specification, and any alterations, modifications, or equivalents of those claims.

All features disclosed in the specification, including the claims, abstracts, and drawings, and all the steps in any method or process disclosed, may be combined in any combination, except combinations where at least some of such features and/or steps are mutually exclusive. Each feature disclosed in the specification, including the claims, abstract, and drawings, can be replaced by alternative features serving the same, equivalent or similar purpose, unless expressly stated otherwise. Thus, unless expressly stated otherwise, each feature disclosed is one example only of a generic series of equivalent or similar features.

It will be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

III. BCMA×CD3 Bispecific Antibodies

CD3 molecule is an important differentiation antigen on T cell membrane and is also a characteristic marker of mature T cells. CD3 molecule consists of four chains of $\gamma$, $\delta$, $\varepsilon$, and $\zeta$, or five chains of $\gamma$, $\delta$, $\varepsilon$, $\zeta$, and $\eta$ ($\zeta$, and $\eta$ are homologous isomers), is composed of three dimers of CD3$\gamma\varepsilon$, CD3$\delta\varepsilon$ and CD3$\zeta\zeta$ (or CD3$\zeta\eta$) and expressed on T cell membrane. Three chains of CD3$\gamma$, $\delta$ and $\varepsilon$ contain highly conserved acidic amino acid residues (glutamic acid in $\gamma$ chain, and aspartic acid in $\delta$ and $\varepsilon$ chains), which can be non-covalently linked to the basic amino acid residues on the $\alpha$ and $\beta$ chains of the T cell receptor (TCR) by a salt bridge to form a stable TCR-CD3 complex structure. The complex can transmit T cell activation signals and stabilize the TCR structure. The intracellular domain of each chain of CD3 contains an ITAM (immune receptor tyrosine-based activation motif) structure, which is the basis for CD3 molecule-mediated intracellular signaling. When the TCR specifically recognizes and binds to an antigen (an antigenic peptide presented by an MHC molecule), tyrosine protein kinases within T cells phosphorylate tyrosine residues on ITAM, and recruit tyrosine protein kinases containing SH2 domains (ZAP-70). The signal is transduced into the cytoplasm of T cells to initiate activation mechanism within the cells. Therefore, CD3 has the function of transmitting the activation signal generated after TCR recognizes the antigen and the signal is the first signal for inducing T cell activation.

B cell maturation antigen (BCMA) is the 17th member of the TNF receptor superfamily. As a non-glycosylated type III transmembrane protein receptor, BCMA consists of 184 amino acid residues with 80 amino acid residues in the intracellular region and only one carbohydrate recognition domain in the extracellular region. BCMA is involved in B cell maturation and differentiation as a specific antigen on the surface of plasma cells. BCMA is also involved in long-term survival of plasma cells as an essential substance. BCMA, TACI and BAFFR respectively bind to two ligands, i.e., a proliferation-inducing ligand (APRIL) and B cell activation factor (BAFF) and participate in activation of signal transduction molecules such as p38, Elk and c-Jun via the NFκB pathway, thereby affecting the maturation, growth and survival of B cells. However, BCMA is not critical for B-cell survival. It has been shown that the production of short-term immunoglobulin, the early humoral immune response and the development of B-lymphocyte in mouse plasma cells after BCMA knockout are not affected (Christine M. Coquery, Loren D. Erickson. Regulatory Roles of the Tumor Necrosis Factor Receptor BCMA. *Crit Rev Immunol.* 2012; 32 (4): 287-305). The expression of BCMA is selective. It is not expressed in naive B cells, memory B cells, CD34+ hematopoietic cells and other normal tissues, and is selectively induced to be expressed during differentiation of plasma cells and is mainly expressed on plasma-like dendritic cells and bone marrow plasma cells.

Disclosed herein is a bispecific antibody comprising an antigen-binding portion against human CD3E. In an aspect, the antigen-binding portion against human CD3E includes a heavy chain CDR 1 (HCDR1) having an amino acid sequence at least about 70% identical to an amino acid sequence as set forth in SEQ ID NO:1. In some embodiments the HCDR1 has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth in SEQ ID NO:1. In some embodiments the HCDR1 has an amino acid sequence 100% identical to an amino acid sequence set forth in SEQ ID NO: 1.

In an aspect, the antigen-binding portion against human CD3E includes a heavy chain CDR 2 (HCDR2) having an amino acid sequence at least about 70% identical to an amino acid sequence as set forth in SEQ ID NO:2. In some embodiments the HCDR2 has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth in SEQ ID NO:2. In some embodiments the HCDR2 has an amino acid sequence 100% identical to an amino acid sequence set forth in SEQ ID NO:2.

In an aspect, the antigen-binding portion against human CD3E includes a heavy chain CDR 3 (HCDR3) having an amino acid sequence at least about 70% identical to an amino acid sequence as set forth in SEQ ID NO:3. In some embodiments the HCDR3 has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth in SEQ ID NO:3. In some embodiments the HCDR3 has an amino acid sequence 100% identical to an amino acid sequence set forth in SEQ ID NO:3.

In an aspect, the antigen-binding portion against human CD3E includes a light chain CDR 1 (LCDR1) having an amino acid sequence at least about 70% identical to an amino acid sequence as set forth in SEQ ID NO:4. In some embodiments the LCDR1 has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth in SEQ ID NO:4. In some embodiments the LCDR1 has an amino acid sequence 100% identical to an amino acid sequence set forth in SEQ ID NO:4.

In an aspect, the antigen-binding portion against human CD3E includes a light chain CDR 2 (LCDR2) having an amino acid sequence at least about 70% identical to an amino acid sequence as set forth in SEQ ID NO:5. In some embodiments the LCDR2 has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth in SEQ ID NO:5. In some embodiments the LCDR2 has an amino acid sequence 100% identical to an amino acid sequence set forth in SEQ ID NO:5.

In an aspect, the antigen-binding portion against human CD3E includes a light chain CDR 3 (LCDR3) having an amino acid sequence at least about 70% identical to an amino acid sequence as set forth in SEQ ID NO:6. In some embodiments the LCDR3 has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth in SEQ ID NO:6. In some embodiments the LCDR3 has an amino acid sequence 100% identical to an amino acid sequence set forth in SEQ ID NO:6; wherein HCDRs and LCDRs are defined according to Kabat.

In a second aspect, there is provided in the present application a bispecific antibody comprising an antigen-binding portion against human BCMA. In an aspect, the antigen-binding portion against human BCMA includes a heavy chain CDR 1 (HCDR1) having an amino acid sequence at least about 70% identical to an amino acid sequence as set forth in SEQ ID NO:7. In some embodiments the HCDR1 has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth in SEQ ID NO:7. In some embodiments the HCDR1 has an amino acid sequence 100% identical to an amino acid sequence set forth in SEQ ID NO: 7.

In an aspect, the antigen-binding portion against human BCMA includes a heavy chain CDR 2 (HCDR2) having an amino acid sequence at least about 70% identical to an amino acid sequence as set forth in SEQ ID NO:8. In some embodiments the HCDR2 has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth in SEQ ID NO:8. In some embodiments the HCDR2 has an amino acid sequence 100% identical to an amino acid sequence set forth in SEQ ID NO:8.

In an aspect, the antigen-binding portion against human BCMA includes a heavy chain CDR 3 (HCDR3) having an amino acid sequence at least about 70% identical to an amino acid sequence as set forth in SEQ ID NO:9. In some embodiments the HCDR3 has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth in SEQ ID NO:9. In some embodiments the HCDR3 has an amino acid sequence 100% identical to an amino acid sequence set forth in SEQ ID NO:9.

In an aspect, the antigen-binding portion against human BCMA includes a light chain CDR 1 (LCDR1) having an amino acid sequence at least about 70% identical to an amino acid sequence as set forth in SEQ ID NO:4. In some embodiments the LCDR1 has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth in SEQ ID NO:4. In some embodiments the LCDR1 has an amino acid sequence 100% identical to an amino acid sequence set forth in SEQ ID NO:4.

In an aspect, the antigen-binding portion against human BCMA includes a light chain CDR 2 (LCDR2) having an amino acid sequence at least about 70% identical to an amino acid sequence as set forth in SEQ ID NO:5. In some embodiments the LCDR2 has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth in SEQ ID NO:5. In some embodiments the LCDR2 has an amino acid sequence 100% identical to an amino acid sequence set forth in SEQ ID NO:5.

In an aspect, the antigen-binding portion against human BCMA includes a light chain CDR 3 (LCDR3) having an amino acid sequence at least about 70% identical to an amino acid sequence as set forth in SEQ ID NO:6. In some embodiments the LCDR3 has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth in SEQ ID NO:6. In some embodiments the LCDR3 has an amino acid sequence 100% identical to an amino acid sequence set forth in SEQ ID NO:6; wherein HCDRs and LCDRs are defined according to Kabat.

In a third aspect, there is provided in the present application a bispecific antibody comprising an antigen-binding portion against human CD3E and an antigen-binding portion against human BCMA.

In an aspect, the antigen-binding portion against human CD3E includes a heavy chain CDR 1 (HCDR1) having an amino acid sequence at least about 70% identical to an amino acid sequence as set forth in SEQ ID NO:1. In some embodiments the HCDR1 has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth in SEQ ID NO:1. In some embodiments the HCDR1 has an amino acid sequence 100% identical to an amino acid sequence set forth in SEQ ID NO:1.

In an aspect, the antigen-binding portion against human CD3E includes a heavy chain CDR 2 (HCDR2) having an amino acid sequence at least about 70% identical to an amino acid sequence as set forth in SEQ ID NO:2. In some embodiments the HCDR2 has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth in SEQ ID NO:2. In some embodiments the HCDR2 has an amino acid sequence 100% identical to an amino acid sequence set forth in SEQ ID NO:2.

In an aspect, the antigen-binding portion against human CD3E includes a heavy chain CDR 3 (HCDR3) having an amino acid sequence at least about 70% identical to an amino acid sequence as set forth in SEQ ID NO:3. In some embodiments the HCDR3 has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth in SEQ ID NO:3. In some embodiments the HCDR3 has an amino acid sequence 100% identical to an amino acid sequence set forth in SEQ ID NO:3.

In an aspect, the antigen-binding portion against human CD3E includes a light chain CDR 1 (LCDR1) having an amino acid sequence at least about 70% identical to an amino acid sequence as set forth in SEQ ID NO:4. In some embodiments the LCDR1 has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth in SEQ ID NO:4. In some embodiments the LCDR1 has an amino acid sequence 100% identical to an amino acid sequence set forth in SEQ ID NO:4.

In an aspect, the antigen-binding portion against human CD3E includes a light chain CDR 2 (LCDR2) having an amino acid sequence at least about 70% identical to an amino acid sequence as set forth in SEQ ID NO:5. In some embodiments the LCDR2 has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth in SEQ ID NO:5. In some embodiments the LCDR2 has an amino acid sequence 100% identical to an amino acid sequence set forth in SEQ ID NO:5.

In an aspect, the antigen-binding portion against human CD3E includes a light chain CDR 3 (LCDR3) having an amino acid sequence at least about 70% identical to an amino acid sequence as set forth in SEQ ID NO:6. In some embodiments the LCDR3 has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth in SEQ ID NO:6. In some embodiments the LCDR3 has an amino acid sequence 100% identical to an amino acid sequence set forth in SEQ ID NO:6; wherein HCDRs and LCDRs are defined according to Kabat.

In an aspect, the antigen-binding portion against human BCMA includes a heavy chain CDR 1 (HCDR1) having an amino acid sequence at least about 70% identical to an amino acid sequence as set forth in SEQ ID NO:7. In some embodiments the HCDR1 has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth in SEQ ID NO:7. In some embodiments the HCDR1 has an amino acid sequence 100% identical to an amino acid sequence set forth in SEQ ID NO:7.

In an aspect, the antigen-binding portion against human BCMA includes a heavy chain CDR 2 (HCDR2) having an amino acid sequence at least about 70% identical to an amino acid sequence as set forth in SEQ ID NO:8. In some embodiments the HCDR2 has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth in SEQ ID NO:8. In some embodiments the HCDR2 has an amino acid sequence 100% identical to an amino acid sequence set forth in SEQ ID NO:8.

In an aspect, the antigen-binding portion against human BCMA includes a heavy chain CDR 3 (HCDR3) having an amino acid sequence at least about 70% identical to an amino acid sequence as set forth in SEQ ID NO:9. In some embodiments the HCDR3 has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth in SEQ ID NO:9. In some embodiments the HCDR3 has an amino acid sequence 100% identical to an amino acid sequence set forth in SEQ ID NO:9.

In an aspect, the antigen-binding portion against human BCMA includes a light chain CDR 1 (LCDR1) having an amino acid sequence at least about 70% identical to an amino acid sequence as set forth in SEQ ID NO:4. In some embodiments the LCDR1 has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth in SEQ ID NO:4. In some embodiments the LCDR1 has an amino acid sequence 100% identical to an amino acid sequence set forth in SEQ ID NO:4.

In an aspect, the antigen-binding portion against human BCMA includes a light chain CDR 2 (LCDR2) having an amino acid sequence at least about 70% identical to an amino acid sequence as set forth in SEQ ID NO:5. In some embodiments the LCDR2 has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth in SEQ ID NO:5. In some embodiments the LCDR2 has an amino acid sequence 100% identical to an amino acid sequence set forth in SEQ ID NO:5.

In an aspect, the antigen-binding portion against human BCMA includes a light chain CDR 3 (LCDR3) having an amino acid sequence at least about 70% identical to an amino acid sequence as set forth in SEQ ID NO:6. In some embodiments the LCDR3 has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth in SEQ ID NO:6. In some embodiments the LCDR3 has an amino acid sequence 100% identical to an amino acid sequence set forth in SEQ ID NO:6; wherein HCDRs and LCDRs are defined according to Kabat.

In some embodiments of the third aspect, the antigen-binding portion against human CD3E and the antigen-binding portion against human BCMA comprise the same light chain variable region.

In some specific embodiments of the third aspect, the antigen-binding portion against human CD3E and the antigen-binding portion against human BCMA comprise the same light chain. This embodiment facilitates proper assembly of the light and heavy chains.

In some embodiments of the third aspect, the bispecific antibody is an IgG1 antibody comprising two heavy chain constant regions having the same hinge region, and the amino acid sequence of the hinge region is shown in SEQ ID NO:15, which replaces the sequences at positions 216-230 of the constant region of the natural human IgG1 antibody; the amino acid position of the antibody constant region is determined according to EU numbering. In some embodiments, the hinge region has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO:15.

In some embodiments of the third aspect, the bispecific antibody is an IgG1 antibody comprising a first heavy chain constant region and a second heavy chain constant region, wherein the amino acids at positions 354 and 366 of the first heavy chain constant region are C and W, respectively, and the amino acids at positions 349, 366, 368 and 407 of the second heavy chain constant region are C, S, A and V, respectively; the amino acid position of the antibody constant region is determined according to EU numbering.

When constructing a bispecific antibody that retains the Fc domain, the structure of the bispecific antibody can be optimized from the following two perspectives: heavy chain heteromerization and proper assembly of the light and heavy chains. In some embodiments, two Fc fragments comprise mutations that can ensure heavy chain heteromerization. The KIH (knob-in-hole) technique is a strategy to address heavy chain heteromerization. Generally, the KIH technique refers to the formation of a structure that facilitates pairing of the heterologous halves to each other by modifying the amino acid sequence of the CH3 region, which can maintain the structure of the normal antibody as much as possible while constituting the bispecific antibody. In some embodiments, the KIH technique utilized includes allowing the amino acids at positions 354 and 366 of one Fc fragment to be C and W, respectively, and the amino acids at positions 349, 366, 368 and 407 of the other Fc fragment to be C, S, A and V, respectively. For guidance on the KIH technique, see, for example, "An efficient route to human bispecific IgG", A. Margaret Merchant et al., Nature Biotechnology, Volume 16, 1998", which is incorporated herein by reference in its entirety.

In some embodiments of the third aspect, the bispecific antibody is an IgG1 antibody comprising a first heavy chain constant region and a second heavy chain constant region, wherein the amino acids at positions 234, 235 and 331 of the first and second heavy chain constant regions are F, E, and S, respectively; the amino acid position of the antibody constant region is determined according to EU numbering.

In some embodiments of the third aspect, the amino acids at positions 234, 235 and 331 of the CH2 fragment of the two heavy chain constant regions are F, E and S, respectively, which can reduce antibody dependent cytotoxicity (ADCC) mediated by the Fc segment of an antibody, thereby potentially reducing side effects caused by bispecific antibody in vivo. For guidance on the above mutations, see, for example, "The binding affinity of human IgG for its high affinity Fc receptor is determined by multiple amino acids in the CH2 domain and is modulated by the hinge region", Stephen M. Canfield et al., J. Exp. Med. Volume 173, 1991, which is incorporated herein by reference in its entirety.

In some embodiments of the first and third aspects, the antigen-binding portion against human CD3E comprises a heavy chain variable region having an amino acid sequence at least about 70% identical to an amino acid sequence as set forth in SEQ ID NO:12 (comprising HCDR1 as set forth in SEQ ID NO:1, HCDR2 as set forth in SEQ ID NO:2, and HCDR3 as set forth in SEQ ID NO:3) and a light chain variable region having an amino acid sequence at least about 70% identical to an amino acid sequence as set forth in SEQ ID NO: 14 (comprising LCDR1 as set forth in SEQ ID NO:4, LCDR2 as set forth in SEQ ID NO:5, and LCDR3 as set forth in SEQ ID NO:6). In some embodiments the heavy chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO:12. In some embodiments, the heavy chain has an amino acid sequence 100% identical to an amino acid sequence set forth as SEQ ID NO:12. In some embodiments the light chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO:14. In some embodiments, the light chain has an amino acid sequence 100% identical to an amino acid sequence set forth as SEQ ID NO: 14.

In some embodiments of the second and third aspects, the antigen-binding portion against human BCMA comprises a heavy chain variable region having an amino acid sequence at least about 70% identical to an amino acid sequence as set forth in SEQ ID NO:10 (comprising HCDR1 as set forth in SEQ ID NO:7, HCDR2 as set forth in SEQ ID NO:8, and HCDR3 as set forth in SEQ ID NO:9) and a light chain variable region having an amino acid sequence at least about 70% identical to an amino acid sequence as set forth in SEQ ID NO: 14 (comprising LCDR1 as set forth in SEQ ID NO:4, LCDR2 as set forth in SEQ ID NO:5, and LCDR3 as set forth in SEQ ID NO:6). In some embodiments the heavy chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO:10. In some embodiments, the heavy chain has an amino acid sequence 100% identical to an amino acid sequence set forth as SEQ ID NO:10. In some embodiments the light chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO:14. In some embodiments, the light chain has an amino acid sequence 100% identical to an amino acid sequence set forth as SEQ ID NO: 14.

In some embodiments of any of the above aspects, the antigen-binding portion against human CD3E comprises a single chain antibody (scfv) or a Fab fragment.

In some embodiments of any of the above aspects, the antigen-binding portion against human BCMA comprises a single chain antibody (scfv) or a Fab fragment.

As the bispecific antibody has two different antigen-binding portions against two different antigens, and the antigen-binding portions may comprise two forms of a single chain antibody (scfv) or a Fab fragment. The configuration of antigen-binding portions of the bispecific antibody may have four combinations for given two antigens: Fab+Fab, Fab+scfv, scfv+Fab, and scfv+scfv.

In some specific embodiments of any of the above aspects, the antigen-binding portion against human CD3E comprises a Fab fragment and the antigen-binding portion against human BCMA comprises a Fab fragment.

In some specific embodiments of any of the above aspects, the antigen-binding portion against human CD3E comprises a Fab fragment and the antigen-binding portion against human BCMA comprises a single chain antibody (scfv).

In some specific embodiments of any of the above aspects, the antigen-binding portion against human CD3E comprises a single chain antibody (scfv) and the antigen-binding portion against human BCMA comprises a Fab fragment.

In some specific embodiments of any of the above aspects, the antigen-binding portion against human CD3E comprises a single chain antibody (scfv) and the antigen-binding portion against human BCMA comprises a single chain antibody (scfv).

The bispecific antibody is also described herein as having two "arms". The bispecific antibody can be divided into two arms bounded by the central axis. The arms of the bispecific antibody can consist of an Fc fragment and an antigen-binding portion (Fab fragment or single chain antibody). For the arm consisting of an Fc fragment and an Fab fragment, its structure is similar to that of a common antibody, comprising intact heavy and light chains, and thus the structure of such an arm can be represented as Fc+Fab, or can be represented as a heavy chain (Fc+the heavy chain variable region of Fab and CH1 fragment)+a light chain (the light chain portion of Fab). When both arms contain the antigen-binding portions in the form of Fab fragment, the structure of the bispecific antibody thus formed is close to that of the native antibody and is a preferred embodiment.

In some embodiments of the third aspect, the antibody has a first arm and a second arm, wherein the first arm comprises an antigen-binding portion against human CD3E and the second arm comprises an antigen-binding portion against human BCMA.

In some embodiments, the first arm comprises a heavy chain variable region that has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, 99%, or 100% identical to an amino acid sequence set forth in SEQ ID NO:12.

In some embodiments, the first arm comprises a heavy chain constant region that has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, 99%, or 100% identical to an amino acid sequence set forth in SEQ ID NO:19.

In some embodiments, the first arm comprises a light chain variable region that has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, 99%, or 100% identical to an amino acid sequence set forth in SEQ ID NO: 14.

In some embodiments, the first arm comprises a light chain constant region that has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, 99%, or 100% identical to an amino acid sequence set forth in SEQ ID NO:20.

In some embodiments, the second arm comprises a heavy chain variable region that has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, 99%, or 100% identical to an amino acid sequence set forth in SEQ ID NO:10.

In some embodiments, the second arm comprises a heavy chain constant region that has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, 99%, or 100% identical to an amino acid sequence set forth in SEQ ID NO: 18.

In some embodiments, the second arm comprises a light chain variable region that has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, 99%, or 100% identical to an amino acid sequence set forth in SEQ ID NO:14.

In some embodiments, the second arm comprises a light chain constant region that has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, 99%, or 100% identical to an amino acid sequence set forth in SEQ ID NO:20.

In an alternative embodiments of the third aspect, the antibody has a first arm and a second arm, wherein the first arm comprises an antigen-binding portion against human CD3E and the second arm comprises an antigen-binding portion against human BCMA.

In some embodiments, the first arm comprises a heavy chain variable region that has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, 99%, or 100% identical to an amino acid sequence set forth in SEQ ID NO: 12.

In some embodiments, the first arm comprises a heavy chain constant region that has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, 99%, or 100% identical to an amino acid sequence set forth in SEQ ID NO:37.

In some embodiments, the first arm comprises a light chain variable region that has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, 99%, or 100% identical to an amino acid sequence set forth in SEQ ID NO: 14.

In some embodiments, the first arm comprises a light chain constant region that has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, 99%, or 100% identical to an amino acid sequence set forth in SEQ ID NO:20.

In some embodiments, the second arm comprises a heavy chain variable region that has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, 99%, or 100% identical to an amino acid sequence set forth in SEQ ID NO:10.

In some embodiments, the second arm comprises a heavy chain constant region that has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, 99%, or 100% identical to an amino acid sequence set forth in SEQ ID NO:38.

In some embodiments, the second arm comprises a light chain variable region that has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, 99%, or 100% identical to an amino acid sequence set forth in SEQ ID NO: 14.

In some embodiments, the second arm comprises a light chain constant region that has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, 99%, or 100% identical to an amino acid sequence set forth in SEQ ID NO:20.

Some embodiments of the bispecific antibody include a bispecific antibody having a first arm and a second arm. In this embodiment, the first arm has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, 99%, or 100% identical to an amino acid sequences set forth in SEQ ID NOs: 39 and 41. In this embodiment, the second arm has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, 99%, or 100% identical to an amino acid sequences set forth in SEQ ID NOs: 40 and 41.

In some embodiments of any of the above aspects, the heavy chain constant region of the bispecific antibody is human IgG1 subtype or various mutants of a selected human IgG1 subtype, such as IgG1H, IgG1K, IgG1m3-H, or IgG1m3-K.

In some embodiments of any of the above aspects, the light chain constant region of the bispecific antibody is human lc subtype or human λ subtype, preferably human lc subtype.

IV. Pharmaceutical Compositions

Also disclosed herein are pharmaceutical compositions comprising the of any one of the aspects disclosed herein and a pharmaceutically acceptable carrier or excipient.

In some embodiments, excipients for use with the compositions disclosed herein include maleic acid, tartaric acid, lactic acid, citric acid, acetic acid, sodium bicarbonate, sodium phosphate, histidine, glycine, sodium chloride, potassium chloride, calcium chloride, zinc chloride, water, dextrose, N-methylpyrrolidone, dimethyl sulfoxide, N,N-dimethylacetamide, ethanol, propylene glycol, polyethylene glycol, diethylene glycol monoethyl ether, and surfactant polyoxyethylene-sorbitan monooleate.

In some embodiments, the compositions further comprise an additional therapeutic agent. In some embodiments, the therapeutic agent is a chemotherapeutic agent. The chemotherapeutic agents can include, among others, cytotoxic agents, anti-metabolite agents (e.g., folate antagonists, purine analogs, pyrimidine analogs, etc.), topoisomerase inhibitors (e.g., camptothecin derivatives, anthracenedione, anthracyclines, epipodophyllotoxins, quinoline alkaloids, etc.), anti-microtubule agents (e.g., taxanes, vinca alkaloids), protein synthesis inhibitors (e.g., cephalotaxine, camptothecin derivatives, quinoline alkaloids), alkylating agents (e.g., alkyl sulfonates, ethylenimines, nitrogen mustards, nitrosoureas, platinum derivatives, triazenes, etc.), alkaloids, terpenoids, and kinase inhibitors.

In some embodiments, the bispecific antibodies and the therapeutic agent are in the same formulation. In some embodiments, the bispecific antibodies and the therapeutic agent are in different formulation. In some embodiments, bispecific antibodies described herein is used prior to the administration of the other therapeutic agent. In some embodiments, bispecific antibodies described herein is used concurrently with the administration of the other therapeutic agent. In some embodiments, bispecific antibodies described herein is used subsequent to the administration of the other therapeutic agent.

Pharmaceutical formulations, in some embodiments, are made to be compatible with a particular local, regional or systemic administration or delivery route. Thus, pharmaceutical formulations include carriers, diluents, or excipients suitable for administration by particular routes. Specific non-limiting examples of routes of administration for compositions herein are parenteral, e.g., intravenous, intra-arterial, intradermal, intramuscular, subcutaneous, intra-pleural, transdermal (topical), transmucosal, intra-cranial, intra-spinal, intra-ocular, rectal, oral (alimentary), mucosal administration, and any other formulation suitable for the treatment method or administration protocol.

In some embodiments, solutions or suspensions used for parenteral application include: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates; and agents for the adjustment of tonicity such as sodium chloride or dextrose. In some embodiments, pH is adjusted with acids or bases, such as hydrochloric acid or sodium hydroxide.

Pharmaceutical formulations for injection include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.), or phosphate buffered saline (PBS). In some embodiments, the carrier is a solvent or dispersion medium containing, for example, water, ethanol, polyol (for example, glycerol, propylene glycol, and liquid polyethylene glycol, and the like), or suitable mixtures thereof. Fluidity is maintained, in some embodiments, for example, by the use of a coating such as lecithin, by the maintenance of the required particle size in the case of dispersion, and by the use of surfactants. Antibacterial and antifungal agents include, for example, parabens, chlorobutanol, phenol, ascorbic acid, and thimerosal. Isotonic agents, for example, sugars; polyalcohols such as mannitol or sorbitol; or sodium chloride, in some embodiments, are included in the composition. In some cases, also included is an agent which delays absorption, in some embodiments, for example, aluminum monostearate or gelatin prolongs absorption of injectable compositions.

In some embodiments, sterile injectable formulations are prepared by incorporating the active composition in the required amount in an appropriate solvent with one or a combination of above ingredients. Generally, dispersions are prepared by incorporating the active composition into a sterile vehicle containing a basic dispersion medium and any other ingredient. In the case of sterile powders for the preparation of sterile injectable solutions, methods of preparation include, for example, vacuum drying and freeze-drying which yields a powder of the active ingredient plus any additional desired ingredient from a previously prepared solution thereof.

For transmucosal or transdermal administration, penetrants appropriate to the barrier to be permeated are used in the formulation. Such penetrants are known in the art, and include, for example, for transmucosal administration, detergents, bile salts, and fusidic acid derivatives. In some embodiments, transmucosal administration is accomplished through the use of nasal sprays, inhalation devices (e.g., aspirators) or suppositories. For transdermal administration, the active compounds are formulated into ointments, salves, gels, creams or patches.

In some embodiments, the pharmaceutical formulations are prepared with carriers that protect against rapid elimination from the body, such as a controlled release formulation or a time delay material such as glyceryl monostearate or glyceryl stearate. The formulations, in some embodiments, are also delivered using articles of manufacture such as implants and microencapsulated delivery systems to achieve local, regional or systemic delivery or controlled or sustained release.

Any suitable route of administration is contemplated for the bispecific antibodies and pharmaceutical compositions disclosed herein. In some embodiments, the bispecific antibody is administered by intravenous administration. In some embodiments, the bispecific antibody is administered by subcutaneous administration. In some embodiments, the bispecific antibody is administered locally. In some embodiments, the bispecific antibody is administered systemically (e.g., intravenously, intramuscularly, subcutaneously, intradermally, orally, intranasally, sublingually). In some embodiments, the bispecific antibody is formulated as a salve, lotion or emulsion. In some embodiments, the bispecific antibody is formulated as a solution. In some embodiments, the bispecific antibody is formulated for topical, oral, buccal, or nasal administration.

In some embodiments, an individual is monitored prior to administration of the bispecific antibody. Symptoms are identified and their severity is assessed. The bispecific antibody as described herein may be administered alone or in combination with additional treatments, singly or multiply over time as discussed herein or known to one of skill in the art. In some embodiments, the individual is monitored such that the efficacy of the treatment regimen is determined. In some embodiments, a treatment regimen is modified in response to preliminary treatment outcomes, such that treatment dose or frequency or dose and frequency is altered so as to attain a desired level of subject response in light of symptom alleviation, side effect reduction, or a combination of symptom alleviation and side effect reduction.

It is to be understood that the foregoing detailed description is intended only to enable those skilled in the art to have better understanding of the present application and is not intended to cause limitations in any way. Various modifications and variations can be made to the described embodiments by those skilled in the art.

The following Examples are for purposes of illustration only and are not intended to limit the scope of the present application.

EXAMPLES

Example 1: Preparation of Recombinant Proteins

Many different recombinant proteins were required in the preparation and identification of CD3ExBCMA bispecific antibody, including the extracellular region of human CD3E (SEQ ID NO: 22), the extracellular region of human CD3D (hCD3D, SEQ ID NO: 23), the extracellular region of monkey CD3E (mfCD3E, SEQ ID NO: 24), the extracellular region of monkey CD3D (mfCD3D, SEQ ID NO: 25), the extracellular region of mouse CD3E (mCD3E, SEQ ID NO: 26), the extracellular region of mouse CD3D (mCD3D, SEQ ID NO: 27) and the extracellular region of human BCMA (hBCMA, SEQ ID NO: 28), the extracellular region of monkey BCMA (mfBCMA, SEQ ID NO: 29), and the extracellular region of mouse BCMA (mBCMA, SEQ ID NO: 30). These recombinant proteins all have a large number of post-translational modifications (e.g., glycosylation or disulfide bonds, etc.), and thus the use of the mammal cell expression system would be more advantageous in maintaining the structures and functions of the recombinant proteins. Furthermore, for ease of purification, His tags (SEQ ID NO: 31) or Fc fragments of mouse antibody IgG2a (mFc, SEQ ID NO: 32) were added to the C-terminus of the non-antibody recombinant proteins, or Fc mutants (FcK, SEQ ID NO: 33 or FcH, SEQ ID NO: 34) of human IgG1 subtype of heterodimer were formed based on KIH (Knob-Into-Hole) technique. In the preparation of recombinant antibody, the heavy chain constant region of the antibody can be human IgG1 subtype (SEQ ID NO: 35) or various mutants of the selected human IgG1 subtype, such as IgG1H (SEQ ID NO: 36), IgG1K (SEQ ID NO: 17), IgG1m3-H (SEQ ID NO: 18) or IgG1m3-K (SEQ ID NO: 19), and the light chain constant region can be human lc subtype (SEQ ID NO: 20) or human X subtype (SEQ ID NO: 21).

Based on the amino acid sequences of various recombinant proteins of interest recorded in the Uniprot database, the genes (comprising His-tag, mFc or Fc encoding gene) of the above recombinant proteins were designed and synthesized. By conventional molecular biology techniques, the synthesized genes encoding the recombinant proteins were cloned into proper eukaryotic expression vectors (e.g., pcDNA3.1 from Invitrogen Inc.). Then, liposomes (e.g., 293fectin from Invitrogen Inc.) or other transfection agents (e.g., PEI) were used to transfect the recombinant protein expression plasmids as prepared into HEK293 cells (e.g., HEK293F from Invitrogen Inc.). The cells were incubated in suspension under serum-free condition for 3-5 days. Then, the supernatant of the culture was harvested by centrifugation.

For recombinant proteins fused with His-tags, the recombinant proteins in the supernatant were further purified using metal chelate affinity chromatography columns (e.g., His Trap FF from GE Inc.). The recombinant proteins and antibodies fused with mFc were further purified using a Protein A/G affinity chromatography column (e.g., Mab select SURE from GE Inc.). Then, the recombinant protein preservation buffer was then replaced with PBS buffer (pH 7.0) or other suitable buffers using a desalination column (e.g., Hitrap desalting, GE Inc.). If necessary, the antibody samples can be sterilized by filtration and then stored in aliquots at −20° C. for later use.

Example 2: Screening and Identification of Common Light Chains 2.1 Screening of Common Light Chains H10B7+L1G10 is a monoclonal antibody that binds to human CD3E obtained by using human antibody library technique. The amino acid sequence of the heavy chain variable region H10B7 of H10B7+L1 G10 is shown in SEQ ID NO: 12 and the amino acid sequence of the light chain variable region L1G10 is shown in SEQ ID NO: 13 (see the amino acid sequences as set forth in SEQ ID NO: 19 and SEQ ID NO: 20 in Chinese Patent Application No. 201910372193.6).

C4 is a monoclonal antibody targeting the tumor antigen BCMA, the amino acid sequence of the heavy chain variable region C4VH is shown in SEQ ID NO: 11, and the amino acid sequence of the light chain variable region C4VK is shown in SEQ ID NO: 16 (see the sequence of the monoclonal antibody CA8-J7M0 in U.S. Pat. No. 9,273,141B2).

The functions and properties of the monoclonal antibodies C4 and H10B7+L1G10 have been experimentally confirmed.

Based on the established dual-vector system for the phage display, the original light chain library was subjected to two rounds of screening and enrichment on the basis of the heavy chain variable region H10B7 of the anti-CD3E monoclonal antibody H10B7+L1G10 with CD3E/CD3D as a screening antigen by using the light chain replacement strategy (see Example 4 in Chinese Patent Application No. 201510097117.0 for detailed experimental protocols). Next, the light chain library enriched by CD3E/CD3D was subjected to two rounds of screening and enrichment on the basis of the heavy chain of the anti-BCMA monoclonal antibody C4 with BCMA as the antigen. Finally, the resultant light chain was identified to obtain the common light chain variable region L9B9 (SEQ ID NO: 14), which can simultaneously maintain the activity of both the anti-CD3E antibody and the anti-BCMA antibody.

The heavy chain variable region H10B7, the heavy chain variable region C4VH of C4, and the light chain variable region L9B9 were respectively cloned into eukaryotic expression vectors fused with human IgG1 heavy chain constant region and the x light chain constant region by using conventional molecular biological means, so as to express complete antibodies H10B7+L9B9 and C4VH+L9B9 in combination.

2.2 Determination of the Binding Affinity of the Anti-BCMA Antibody C4VH+L9B9 with Common Light Chain to Human BCMA.

The affinity of anti-BCMA antibodies (C4 and C4VH+L9B9) was determined by surface plasmon resonance technique using Biacore X100. Reagents and consumables such as amino coupling kit (BR-1000-50), human antibody capture kit (BR-1008-39), CM5 chip (BR100012), and 10×HBS-EP, pH 7.4 (BR100669) were purchased from GE healthcare. The surface of the carboxylated CM5 chip was activated with 1-ethyl-3-(3-dimethylaminopropyl) carbodiimide hydrochloride (EDC) and N-hydroxysuccinimide (NHS) according to the instructions in the kit. The anti-human IgG (Fc) antibody (capture antibody) was diluted to 25 μg/mL with 10 mM sodium acetate solution (pH 5.0), followed by injection at a flow rate of 10 μL/min to achieve a coupling amount of approximately up to 10,000 response units (RU). After injection of the capture antibody, 1 M ethanolamine was injected to block unreacted groups. For kinetic measurement, the anti-BCMA antibody was diluted to 0.5-1 μg/mL, followed by injection at a flow rate of 10 μL/min to ensure that about 400 RU of the antibody was captured by the anti-human Fc antibody. Next, a series of concentration gradients for hBCMA-his were set (for example, 0.617 nM, 1.85 nM, 5.56 nM, 16.7 nM, and 50 nM), and were injected from low concentration to high concentration at 30 μL/min at 25° C. The association time was 120 s, and the dissociation time was 1800 s. The surface of the chip was regenerated by injection of 3 M $MgCl_2$ solution at 10 μL/min for 30 s. The association rate (Kon) and dissociation rate (Koff) were calculated by fitting the association and dissociation sensorgrams with a 1:1 association model using the Biacore X100 evaluation software, version 2.0.1. The dissociation equilibrium constant (KD) was calculated as the ratio Koff/Kon. The fitting results are shown in Table 1.

TABLE 1

| Affinity constants of binding of anti-BCMA antibodies to human BCMA | | | |
| --- | --- | --- | --- |
| | Kon | Koff | KD |
| C4 | 4.333E+5 | 7.948E−5 | 1.834E−10 |
| C4VH + L9B9 | 3.238E+5 | 9.554E−4 | 2.950E−9 |

Example 3: The Affinity Maturation of Anti-BCMA Antibody 3.1 Screening of the Heavy Chain Mutation Library of C4

A CDR3 mutant library based on the heavy chain variable region C4VH was constructed by introducing a mutation in the CDR3 region of the heavy chain variable region C4VH using conventional molecular biological means. The designed mutation scheme is shown in Table 2, and the 1.2×10E8 of library capacity was created with an accuracy of 86.7%.

TABLE 2

| Mutation scheme of CDR3 mutant library based on the heavy chain variable region C4VH of C4 C4VH-CDR3: 1.8 × 10E7 diversity | | |
| --- | --- | --- |
| Initial amino acid | Mutant amino acid | Degenerate code |
| G | Q A or D | GVT |
| A | A, T, N, D, S or G | RVC |
| I | L, F, I or V | NTC |
| Y | F, S, Y, I, T or N | WHC |
| D | D, Y, S or A | KMC |
| G | Q A or D | GVT |
| Y | For Y | TWC |
| D | D, E, A or G | GVM |
| V | L, F, I or V | NTC |
| L | L, F, I or V | NTC |
| D | D, N, S, T, A or G | RVC |
| N | N, D, Y, S, A or T | DMC |

Based on the dual-vector system for the phage display (see Example 5 in Chinese Patent Application No. 201510097117.0), the constructed C4VH-CDR3 mutant library was subjected to three rounds of screening and enrichment with the hBCMA-His antigen by solid phase screening method. Finally, the heavy chain variable region mutant H13F1 (SEQ ID NO:10) with increased affinity was obtained.

25

3.2 Affinity Assay of the Heavy Chain Mutant of C4

The nucleotide sequences encoding the heavy chain variable region mutant H13F1 of C4 and the light chain variable region L9B9 were respectively cloned into eukaryotic expression vectors fused with the nucleotide sequences encoding the human heavy chain constant region and the light chain constant region by using conventional molecular biological means, so as to express complete antibodies in combination. Referring to Example 2.2, the mutant of C4 (IgG1 subtype) was subjected to affinity assay by using Biacore X100, and the result is shown in Table 3.

TABLE 3

Affinity constants of binding of anti-BCMA antibodies to human BCMA

| | Kon | Koff | KD |
|---|---|---|---|
| C4VH + L9B9 | 5.307E+5 | 8.156E-4 | 1.537E-9 |
| H13F1 + L9B9 | 7.85E+5 | 4.284E-4 | 5.429E-10 |

Example 4: Preparation of Bispecific Antibodies

The nucleotide sequences encoding the heavy chain variable region H10B7 of the anti-CD3E monoclonal antibody and the heavy chain variable region H13F1 of the anti-BCMA monoclonal antibody were respectively cloned into suitable eukaryotic expression vectors to construct heterodimers based on the common light chain. That is, the nucleotide sequence encoding the heavy chain variable region of the anti-CD3E antibody was cloned into eukaryotic expression vectors fused with the nucleotide sequence encoding the IgG1 constant region with Knob mutation IgG1m3-K, the nucleotide sequence encoding the heavy chain variable region of the anti-BCMA antibody was cloned into eukaryotic expression vectors containing the nucleotide sequence encoding the IgG1 constant region with Hole mutation IgG1m3-H, and the nucleotide sequence encoding the variable region VK of the common light chain L9B9 was cloned into eukaryotic expression vectors fused with the nucleotide sequence encoding the human light chain constant region CK.

The three constructed eukaryotic expression vectors expressing H10B7-IgG1m3-K, H13F1-IgG1m3-H and L9B9VK-CK were co-transfected into HEK293F cells using liposomes, and the cells were cultured in suspension in a serum-free medium for 3-5 days. The supernatant of the culture was harvested by centrifugation. The bispecific antibodies in the culture supernatant were purified using a Protein A/G affinity chromatography column (e.g., Mabselect SURE, GE Inc.). The recombinant protein preservation buffer was then replaced with PBS buffer (pH 7.0) or other suitable buffers using a desalination column (e.g., Hitrap desaulting, GE Inc.). The desalted protein solution was purified by a size exclusion chromatography (SEC) using Superdex200 (GE), thereby obtaining the protein of interest. If necessary, the antibody samples can be sterilized by filtration and then stored in aliquots at −20° C. for later use.

Example 5: Affinity Assay of Bispecific Antibodies

The affinity assays were performed on anti-BCMA monoclonal antibody H13F1+L9B9, anti-CD3E monoclonal antibody H10B7+L9B9, and bispecific antibody CD3ExBCMA by surface plasmon resonance technique using Biacore X100.

When the affinity of the anti-BCMA monoclonal antibody and the CD3ExBCMA bispecific antibody to the BCMA antigen was determined, the anti-human IgG (Fc) antibody was conjugated to the surface of the CM5 chip. The antibody protein was diluted to 0.5-1 μg/ml, and was injected at 10 μL/min. About 400 RU of the BCMA monoclonal antibody was ensured to be captured by the anti-human Fc antibody, and about 800 RU of the bispecific antibody CD3ExBCMA was ensured to be captured by the anti-human Fc antibody. Next, a series of concentration gradients for BCMA-his were set (for example, 0.617 nM, 1.85 nM, 5.56 nM, 16.7 nM, and 50 nM), and were injected from low concentration to high concentration at 30 μL/min at 25° C. The association time was 120 s, and the dissociation time was 1800 s. The surface of the chip was regenerated by injection of 3 M $MgCl_2$ solution at 10 μL/min for 30 s. The results of affinity fit are shown in Table 1 and Table 2.

TABLE 1

Affinity constants of binding of anti-BCMA monoclonal antibody H13F1 + L9B9 and the bispecific antibody CD3xBCMA to human BCMA

| | Kon | Koff | KD |
|---|---|---|---|
| H13F1 + L9B9 | 1.174E+6 | 4.161E-4 | 3.544E-10 |
| CD3ExBCMA | 1.063E+6 | 3.236E-4 | 3.045E-10 |

TABLE 2

Affinity constants of binding of anti-BCMA monoclonal antibody H13F1 + L9B9 and the bispecific antibody CD3xBCMA to monkey BCMA

| | Kon | Koff | KD |
|---|---|---|---|
| H13F1 + L9B9 | 6.63E+5 | 3.289E-3 | 4.961E-9 |
| CD3ExBCMA | 6.551E+5 | 3.26E-3 | 4.976E-9 |

When the affinity of the anti-CD3E monoclonal antibody and the bispecific antibody CD3ExBCMA to the CD3E antigen was determined, the anti-human Fab antibody (Human Fab Capture Kit, GE, 28-9583-25) was conjugated to the surface of the CM5 chip. The antibody protein was diluted to 0.5-1 μg/ml, and was injected at 10 μL/min. About 70 RU of the anti-CD3E monoclonal antibody was ensured to be captured by the anti-human Fab antibody, and about 150 RU of the bispecific antibody CD3ExBCMA was ensured to be captured by the anti-human Fab antibody. A series of concentration gradients for human CD3E heterodimer CD3E-FcK/CD3D-FcH were set (for example, 12.5 nM, 25 nM, 50 nM, 100 nM, and 200 nM), and were injected from low concentration to high concentration at 30 μL/min at 25° C. The association time was 120 s, and the dissociation time was 600 s. The surface of the chip was regenerated by injection of 10 mM glycine-HCl (pH 2.1) at 10 μL/min for 60 s. The results of affinity fit are shown in Table 3.

TABLE 3

Affinity constants of binding of anti-CD3E monoclonal antibody H10B7 + L9B9 and the bispecific antibody CD3ExBCMA to human CD3E

| | Kon | Koff | KD |
|---|---|---|---|
| H10B7 + L9B9 | 1.750E+5 | 3.075E-3 | 1.757E-8 |
| CD3ExBCMA | 1.179E+5 | 2.838E-3 | 2.408E-8 |

Example 6: Identification of the Ability of Bispecific Antibodies to Simultaneously Recognize Both CD3E and BCMA Antigens The ability of the bispecific antibody CD3ExBCMA (CD3ExBCMA BsAb) to simultaneously bind to both CD3E and BCMA antigens was detected using conventional ELISA methods.

A 96-well ELISA plate was coated with CD3E-FcK/CD3D-FcH antigen (3 μg/mL, 100 μL/well), and was coated overnight in a refrigerator at 4° C. After being blocked with blocking solution PBS-0.1% Tween 20-3% milk at 37° C. for 1 hour, the anti-BCMA monoclonal antibody H13F1+L9B9, the anti-CD3E monoclonal antibody H10B7+L9B9 and the bispecific antibody CD3ExBCMA (10 μg/mL, 100 μL/well) were respectively added to the plate in duplicate, and incubated at 37° C. for 1 hour. The ELISA plate was washed with PBS-0.1% Tween 20, followed by addition of BCMA-His antigen (1 μg/mL, 100 μL/well) and incubation at 37° C. for 1 hour. The ELISA plate was washed with PBS-0.1% Tween 20, followed by addition of HRP mouse anti-his IgG (Beijing ComWin Biotech Co., Ltd., cw0285M) and incubation at 37° C. for 1 hour. The ELISA plate was washed with PBS-0.1% Tween 20, and OPD substrate color development solution was added. The color development was terminated with 1 M H2SO4 after 5-10 minutes. The optical density value at 492 nm/630 nm dual wavelength was measured using a microplate reader. The result of ELISA assay is shown in FIG. 2. The bispecific antibody CD3ExBCMA can simultaneously recognize both CD3E and BCMA antigens.

Figure 3:
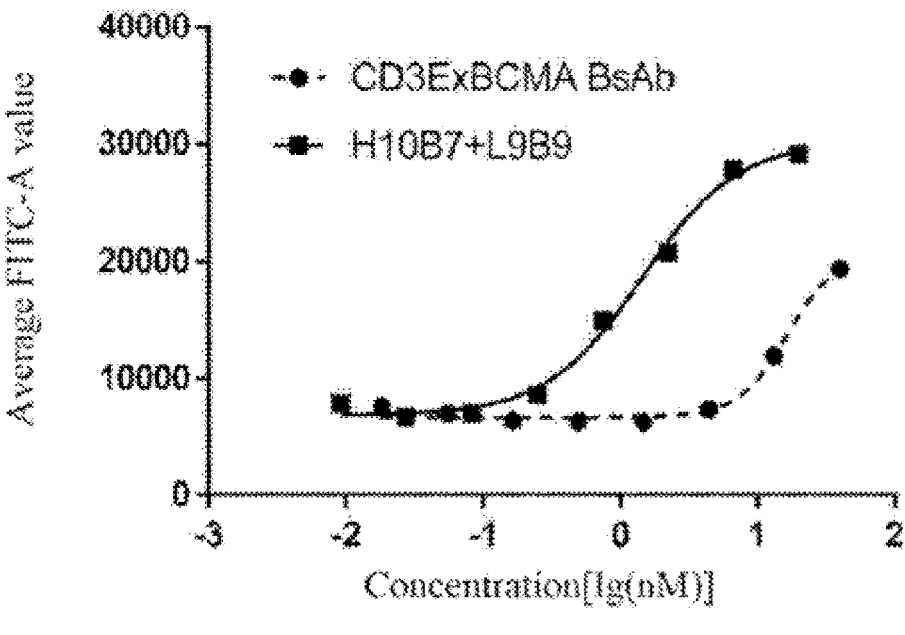
FIG. 3 shows the results of analyzing the binding of the bispecific antibody CD3ExBCMA to CD3E on the surface of Jurkat human acute T lymphocyte leukemia cell by using flow cytometry.

Example 7: Identification of the Ability of Bispecific Antibodies to Recognize CD3E and BCMA on Cell Surfaces Jurkat human acute T-lymphocyte leukemia cells (Cell Resource Center, Institute of Basic Medicine, Chinese Academy of Medical Sciences) in the logarithmic growth phase were harvested, centrifuged, and resuspended in PBS buffer containing 1% BSA to $2\times10^6$ cells/mL, and plated at 100 μL/well in 96-well V bottom plates. The anti-CD3E monoclonal antibody H10B7+L9B9 and the bispecific antibody CD3ExBCMA were taken for gradient dilution. The anti-CD3E monoclonal antibody had an initial concentration of 3 μg/mL, and was diluted by 3-fold gradient, with a total of 8 concentration points. The bispecific antibody had an initial concentration of 6 μg/mL, was diluted by 3-fold gradient, with a total of 8 concentration points. 100 μL of the anti-CD3E monoclonal antibody or 100 μL of the bispecific antibody was added to the wells containing cells and incubated at 4° C. for 1 hour. Next, the cells were washed three times with 200 μL of PBS solution and incubated with goat anti-human IgG-FITC (Beijing Zhongshan Golden Bridge Biotechnology Co., Ltd., ZF-0308) (100 μL/well) at 4° C. for 30 minutes in the dark. Next, the cells were washed three times with 200 μL of PBS solution, and suspended in 100 μL of PBS solution. Thereafter, the FITC channel was detected by flow cytometer (ACEA, Novocyte). The results showed that the bispecific antibody CD3ExBCMA can bind well to CD3 positive Jurkat cells (FIG. 3). The KD value of the bispecific antibody CD3ExBCMA was 16.79 nM, and the KD value of the anti-CD3E monoclonal antibody was 1.43 nM.

Figure 4:
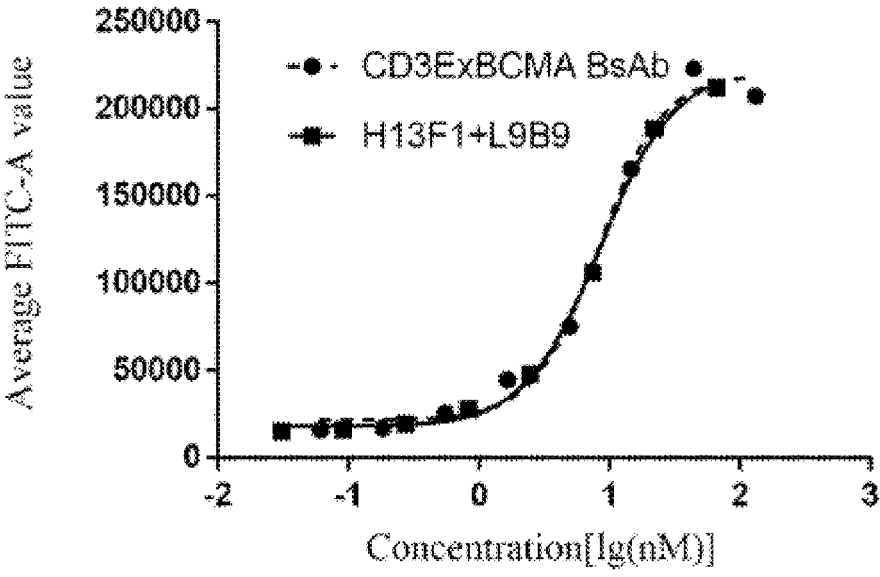
FIG. 4 shows the results of analyzing the binding of the bispecific antibody CD3ExBCMA to BCMA on the surface of NCI-H929 human plasma cell leukemia cell by using flow cytometry.

NCI-H929 human plasma cell leukemia cells (Cell Resource Center, Institute of Basic Medicine, Chinese Academy of Medical Sciences) in logarithmic growth phase were harvested, centrifuged, and resuspended in PBS buffer containing 1% BSA to $2\times10^6$ cells/mL, and plated at 100 μL/well in 96-well V bottom plates. The anti-BCMA monoclonal antibody H13F1+L9B9 and the bispecific antibody CD3ExBCMA were taken for gradient dilution. The anti-BCMA monoclonal antibody had an initial concentration of 10 μg/mL, was diluted by 3-fold gradient, with a total of 8 concentration points. The bispecific antibody had of an initial concentration of 20 μg/mL, was diluted by 3-fold gradient, with a total of 8 concentration points. 100 μL of the anti-BCMA monoclonal antibody or 100 μL of the bispecific antibody was added to the wells containing cells and incubated at 4° C. for 1 hour. Next, the cells were washed three times with 200 μL of PBS solution and incubated with goat anti-human IgG-FITC (Beijing Zhongshan Golden Bridge Biotechnology Co., Ltd., ZF-0308) (100 μL/well) at 4° C. for 30 minutes in the dark. Next, the cells were washed three times with 200 μL of PBS solution, and suspended in 100 μL of PBS solution. Thereafter, the FITC channel was detected by flow cytometer (ACEA, Novocyte). The results showed that the bispecific antibody CD3ExBCMA can bind well to BCMA positive NCI-H929 cells (FIG. 4). The KD value of the bispecific antibody CD3ExBCMA was 8.27 nM, and the KD value of the anti-BCMA monoclonal antibody was 8.47 nM.

Figures 5, 6:
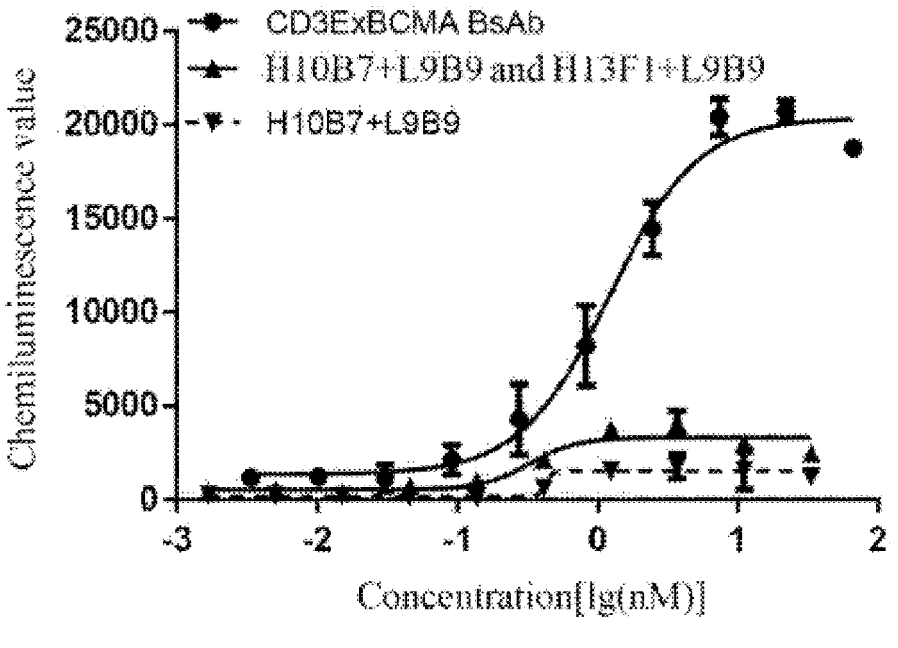
FIG. 5 shows the specific activation of jurkat-dual cells by BCMA-positive tumor cells mediated by the bispecific antibody CD3ExBCMA.
FIG. 6 shows the killing effect of PBMC on BCMA-positive tumor cells mediated by the bispecific antibody CD3ExBCMA.

Example 8: Bispecific Antibody Mediates Specific Activation of Jurkat-Dual Cells by BCMA Positive Tumor Cells NCI-H929 human plasma cell leukemia cells (high expression of BCMA, purchased from Cell Resource Center, Institute of Basic Medicine, Chinese Academy of Medical Sciences) in logarithmic growth phase were collected. After centrifugation, the cells were resuspended with 1640 medium to $4\times10^5$ cells/mL and plated in the cell plate at 50 μL/well. Jurkat-dual cells (purchased from Invivogen) in logarithmic growth phase were collected, centrifugated, and resuspended with 1640 medium to $1\times10^6$ cells/mL, and were added to the cell plate with 100 μL/well to obtain a final E:T ratio of 5:1. The bispecific antibody CD3ExBCMA (50 μL/well), the anti-CD3E monoclonal antibody H10B7+L9B9 (50 μL/well) or a combination of the anti-CD3E monoclonal antibody H10B7+L9B9 and the anti-BCMA monoclonal antibody H13F1+L9B9 was then added to the cell plate, wherein the bispecific antibody had an initial concentration of 10 μg/mL, and was diluted by 3-fold gradient, with a total of 10 concentration point; the anti-CD3E monoclonal antibody H10B7+L9B9 had an initial concentration of 5 μg/mL, and was diluted by 3-fold gradient, with a total of 10 concentration points; and for the combination of the anti-CD3E monoclonal antibody H10B7+L9B9 and the anti-BCMA monoclonal antibody H13F1+L9B9, each of which had an initial concentration of 5 μg/mL, and was diluted by 3-fold gradient, with a total of 10 concentration points. After 20 hours of incubation, the supernatant was taken and the specific activation of Jurkat-Dual cells by BCMA-positive tumor cells mediated by the bispecific antibody CD3ExBCMA, the anti-CD3E monoclonal antibody, and the combination of the anti-CD3E monoclonal antibody and the anti-BCMA monoclonal antibody were detected and analyzed with reference to the instructions of QUANTI-LucTM (QUANTI-LucTM, Invivogen, rep-qlc2). The results show that only the bispecific antibody CD3ExBCMA can mediate activation of Jurkat-Dual cells by BCMA-positive tumor cells, and neither anti-CD3E monoclonal antibody alone nor the combination of anti- CD3E monoclonal antibody and anti-BCMA monoclonal antibody can mediate activation of Jurkat-Dual cells by BCMA-positive tumor cells (FIG. 5).

Example 9: Bispecific Antibody Mediates the Killing of BCMA Positive Tumor Cells by T Cells 9.1 Isolation of Human Peripheral Blood Mononuclear Cells (PBMCs)

Blood (50 mL each) was collected from normal volunteers. The collected blood was provided by the inventors and their colleagues as volunteers, all of whom had signed informed consent. Inclusion criteria for volunteers were as follows:

Age older than 18 years;

No HIV and HBV infection;

Normal blood routine test;

Non-pregnant or non-lactating women.

PBMCs were isolated from whole blood of the volunteers using Ficoll density gradient centrifugation and were cultured in 1640 medium.

9.2 Detection of PBMCs Killing BCMA Positive Tumor Cells Mediated by Bispecific Antibody NCI-H929 human plasma cell leukemia cells (high expression of BCMA), RPMI-8226 human multiple myeloma cells (moderate expression of BCMA), and HL60 human acute promyelocytic leukemia cells (BCMA negative) were purchased from the Cell Resource Center, Institute of Basic Medicine, Chinese Academy of Medical Sciences. The cells in the logarithmic growth phase were collected, centrifuged, and resuspended in 1640 medium to $4\times10^5$ cells/mL, and were plated in cell plates at 50 μL/well. Next, the bispecific antibody CD3ExBCMA, which had an initial concentration of 1ug/mL and was diluted by 4-fold gradient with a total of 10 concentration points, was added (50 μL/well) to the cell plate. Finally, 100 μL/well of PBMCs (effectors) were added to obtain a final ET ratio of 5:1. Meanwhile, target cell control alone (NCI-H929 cells, RPMI-8226 cells, or HL60 cells), effector cell control alone (PBMCs), and medium blank control alone were set and the volumes thereof were replenished to 200 μL with medium. After 20 hours of incubation, the supernatant was taken. The killing rate of T cells to tumor cells mediated by the bispecific antibody was detected and analyzed with reference to the instructions of the cytoTox96® Non-Radioactive Cytotoxicity Assay (Promega, G1780).

The results showed that in the presence of the bispecific antibody CD3ExBCMA, the effector cells had a significant killing effect on the highly expressed NCI-H929 cells and the moderately expressed RPMI-8226 cells, but had no killing effect on the negative HL60 (FIG. 6), indicating that the bispecific antibody CD3ExBCMA can effectively mediate the killing of T cells to cells with different positive expression levels of BCMA, and cannot mediate the killing of BCMA negative cells.

Example 10: Bispecific Antibodies can Specifically Stimulate the Expression of Activation Molecule on the Surface of T Cells NCI-H929 human plasma cell leukemia cells (high expression of BCMA), RPMI-8226 human multiple myeloma cells (moderate expression of BCMA), and HL60 human acute promyelocytic leukemia cells (BCMA negative) in logarithmic growth phase were collected, centrifuged, and resuspended in 1640 medium to $4\times10^5$ cells/mL, and were plated in cell plates at 50 μL/well. Next, the bispecific antibody CD3ExBCMA, which had an initial concentration of 1ug/mL and was diluted by 4-fold gradient with a total of 10 concentration points, was added (50 μL/well) to the cell plate. Finally, 100 μL/well of PBMCs (effectors) were added to obtain a final E:T ratio of 5:1. After 20 hours of incubation, the cells were centrifuged at 350 g for 5 minutes, washed once with PBS, and incubated with flow cytometry antibodies, i.e., anti-human CD3 (Ebioscience, 17-0037-42) and anti-human CD69 (Ebioscience, 11-0069-42) at 4° C. for 30 minutes in the dark. Then the cells were washed twice with 200 μL PBS solution, resuspended in 100μ·L PBS solution and detected by flow cytometer (ACEA, Novocyte) to compare the difference in the expression of the activation marker CD69 of the CD3 positive cell population after treatment with the bispecific antibody CD3ExBCMA.

Figure 7:
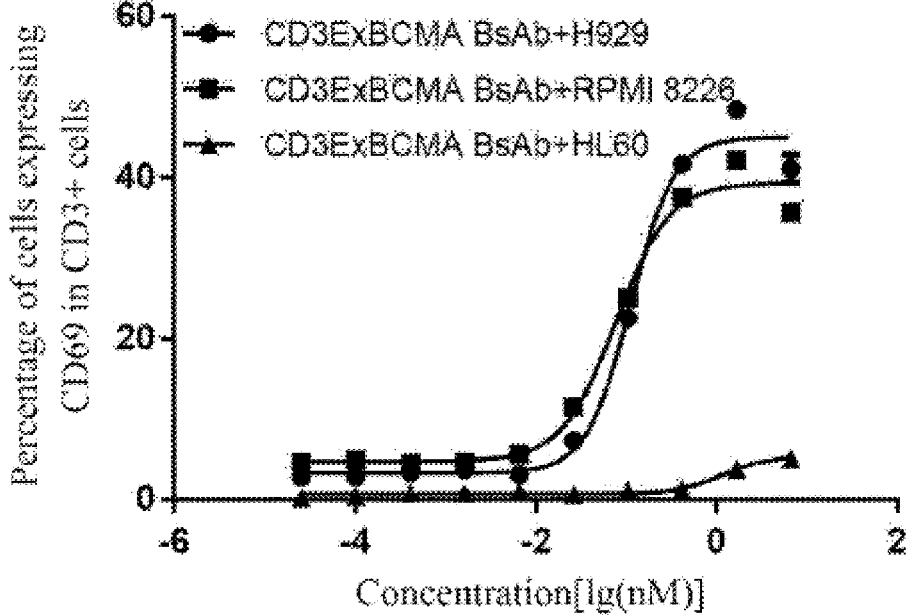
FIG. 7 shows the results of the bispecific antibody CD3ExBCMA stimulating CD69 expression on the surface of T cells in the presence of BCMA-positive tumor cells.

The results showed that the bispecific antibody CD3ExBCMA can specific activate T cells in the presence of NCI-H929 with high expression of BCMA or RPMI-8226 with moderate expression of BCMA, and the bispecific antibody CD3ExBCMA cannot activate T cells in the presence of FIL60 with negative BCMA (FIG. 7), indicating that the bispecific antibody CD3ExBCMA can effectively activate T cells in the presence of cells with different positive expression levels of BCMA, and cannot activate T cells in the presence of BCMA negative cells.

Example 11: GR1803 Characterization

GR1803 is a novel recombinant humanized anti-CD3/BCMA bispecific monoclonal antibody with common light chains developed based on the Knob into Hole (KIH) technology platform. There are two identical kappa light chains with 214 amino acid residues in each, with a theoretical molecular weight of 23.4 kDa. There are two asymmetric IgG1 heavy chains of different sequences. The Knob structure targets CD3 antigen (also referred to as anti-CD3) and has 445 amino acid residues and a theoretical molecular weight of 50.5 kDa. The hole structure targets BCMA antigen (also referred to as anti-BCMA) and has 448 amino acids and a theoretical molecular weight of 50.4 kDA. In the intact molecule, there are 2 N-glycosylation sites, located at $N_{295}$ position of the heavy chain anti-CD3 and $N_{298}$ position of the heavy chain anti-BCMA, respectively; there are 17 pairs of disulfide bonds linked in the form of IgG1. GR1803 can activate T cells by specifically binding to CD3 on the surface of T cells and BCMA on the surface of tumor cells.

The intact molecular mass of an exemplary lot of GR1803 is 147853.38 Da. The molecular mass of an exemplary lot of the deglycosylated GR1803 is 144964.67 Da. In an exemplary lot, the molecular mass the reduced light chain is 23434.546 Da. In an exemplary lot, the molecular mass of the reduced anti-CD3 heavy chain is 50532.65 Da. In an exemplary lot, the molecular mass of the reduced anti-BCMA heavy chain is 50449.05 Da. In an exemplary lot, the molecular mass of the deglycosylated anti-CD3 heavy chain is 49088.30 Da. In an exemplary lot, the molecular mass of the deglycosylated anti-BCMA heavy chain is 49004.70 Da.

Two lots of GR1803 were prepared and then characterized based on protein content (UV, isoelectric point (capillary isoelectric focusing), purity (reduced and non-reduced CD-SDS), and activity (double antigen sandwich ELISA and reporter gene method). Critical quality attributes (CQAs) and critical production parameters (CPPs) of the product, including, but not limited to, pH value, elution method, load, retention time, peak collection criteria in chromatography procedures during purification, pH value and duration of low pH inactivation process; pressure in depth filtration and virus filtration, have been preliminary determined.

Capillary isoelectric focusing (cIEF) can focus and separate protein components with different changes in samples according to their isoelectric points in a certain pH gradient electrolyte. Different protein components are focused at the pH position corresponding to their respective isoelectric points to form separated protein focused bands. By adding two markers (pl markers) with known isoelectric points to the sample and focusing at the same time, the isoelectric point of the sample to be tested can be calibrated. The pI value of the main peak is the isoelectric point of the sample.

Beckman-Coulter PA800 plus capillary electrophoresis instrument was used with neutral-coated electrophoresis capillary to analyze the isoelectric point of two lots of GR1803 drug substance. The isoelectric points of the two lots of GR1803 drug substance were both 9.0 as shown in Table 7. However, the isoelectric peak may range from 8.5 to 9.5.

TABLE 7 cIEF results of two lots of GR1803 drug substances

| Sample name | Lot number | Isoelectric point (main peak pI) |
|---|---|---|
| GR1803 drug substance | 1 | 9.0 |
| | 2 | 9.0 |

The secondary structures content of the two lots of GR1803 drug substance are: $\alpha$-helix: 6.8%, $\beta$-fold (antiparallel): 48.7%~48.9%, $\beta$-fold (parallel): 4.0%, $\beta$-corner: 14.7%, irregular curl: 30.0%-30.1%.

The characteristic peak wavelengths of the second derivative UV absorption spectrum of GR1803 drug substance were 287.6 nm and 294.7 nm, and the characteristic valley wavelengths were 283.4 nm and 290.6 nm. The maximum emission wavelengths of GR1803 drug substance of 280 nm excitation wavelength were 355-356 nm, and the maximum emission wavelengths at 295 nm and excitation wavelength were 353-354 nm.

The melting temperature Tm of GR1803 drug substance was about 61° C., which implies good thermal stability. The pH is 4.8-5.8.

The main glycoform of GR1803 drug substance was A2G0F, with the proportion of 76.3%-77.1%; The proportion of nonfucosylated glycoform A2G0 was 2.5%; The high mannose glycoform A2G1F 2.9%-3.0%; the galactosylated glycoform A2G1F accounts for 9.8%-10.2%, A2G2F accounts for 1.4%, and A3G1F accounts for 0.5%; the other glycoforms A1G0F accounts for 2.1%-2.2%, and A3G0F accounts for 1.8%-2.0%.

The deamidation modification of GR1803 drug substance mainly occurs at the HC (anti-BCMA) $N_{316}$/HC (anti-CD3) $N_{313}$, HC (anti-BCMA) $N_{362}$, $N_{385}$, HC (anti-BCMA) $N_{390}$/HC (anti-CD3) $N_{387}$, HC (anti-BCMA) $N_{435}$/HC (anti-CD3) $N_{437}$, with the proportion of 2.2%-2.3%, 1.2%, 1.5%, 6.1%-6.2%, 2.6-2.7%, respectively.

Oxidative modification mainly occurs at LC $M_4$, HC (anti-BCMA) $M_{34, 162}$ of heavy chain, HC (anti-BCMA) $M_{253}$/HC (anti-CD3) $M_{250}$, HC (anti-BCMA) $M_{429}$, HC (anti-CD3) $M_{100}$ and 426, with the proportions of 0.1%, 0.5%-0.6%, 0.3%, 4.2%-5.1%, 0.8%-0.9%, 9.5%-11.4%, and 0.3% respectively.

HC (anti-BCMA) $D_{281}$ was isomerically modified, with the proportion of 0.1%-0.2%.

The proportion of N-terminal glutamine cyclization to pyroglutamic acid of heavy chain (anti-BCMA) was 98.2%, and that of heavy chain (anti-CD3) was 99.9%.

The proportion of non-clipped lysine at C-terminal of heavy chain was 4.6%-5.2%, and the proportion of proline amidation at C-terminal was 2.7%-3.9%.

Glycation modifications were detected at several lysine residue sites, all of which were less than 1%.

The HC (anti-BCMA) $N_{298}$/HC (anti-CD3) $N_{295}$ occurred glycosylation modification. The main glycanform was A2G0F, with the proportion of 73.0%-73.5%.

The released purity of monomer of two lots of drug substances were 99.8% and the proportion of aggregate were 0.2%. The released proportion of acidic peaks of the two lots of drug substance were 13.2% and 11.4%, the proportion of main peaks were 68.4% and 69.7%, and the proportion of basic peaks were 18.5% and 18.9%.

The release purity of IgG main peak detected of the two lots of drug substance were 94.5% and 94.4% and the proportion of fragments were 5.5% and 5.6%.

The released sum of the light chain and heavy chain contents of the two lots of drug substance was 99.4% and 94.6%, and the proportion of impurity fragments was 0.6% and 0.4%.

The proportions of pre-main peaks of peaks of the two lots of drug substances were 13.0% and 12.3%, the proportions of main peaks were 80.8% and 80.1%, and the proportions of post-major peaks were 6.2% and 7.6%.

The affinity constant KD of two lots of drug substance to CD3D & CD3E antigen were $1.261 \times 10^{-7}$M and $2.412 \times 10^{-7}$M.

The affinity constant KD of two lots of drug substance to BCMA-his antigen were $5.405 \times 10^{-10}$ M and $4.880 \times 10^{-10}$ M.

The two lots of drug substance can bind to FcRn under acidic conditions and the affinity constant KD were $9.243 \times 10^{-5}$ M and $7.917 \times 10^{-5}$ M. The $EC_{50}$ values of the two lots of drug substance binding to FcRn were 2.405 μg/ml and 2.455 μg/ml, respectively. Under neutral conditions, there was no obvious binding.

The GR1803 drug substance can bind to CD3D & CD3E and BCMA-his antigen simultaneously and the binding activity $EC_{50}$ values of two lots of drug substance were 8.183 μg/ml and 3.224 μg/ml, respectively.

The GR1803 drug substance can engage T cells with BCMA positive tumor cells in vitro and activate T cells. The activity $EC_{50}$ values of two lots of GR1803 drug substance were 0.045 μg/ml and 0.049 μg/ml, respectively.

After two lots of GR1803 were stored at different temperatures ($\leq$-60° C. and -40° C.±5° C.) for 12 months, the protein content and purity basically remained unchanged, the amounts of improperly paired H and K impurity residues were all below the LOQ, and there were no significant changes in the binding activity and cell biological activity.

Sequence Listing

| SEQ ID NO | Amino Acid Sequence |
|---|---|
| 1 | GYGMH |
| 2 | VIWFDGSRKYYVDSVKG |
| 3 | QMGYWHFGL |

-continued

| Sequence Listing | |
| --- | --- |
| SEQ ID NO | Amino Acid Sequence |

4     RASQSISNYLT

5     EASSRPS

6     QQWSRLPVT

7     NYWMH

8     ATYRGHSDTYYNQKFKG

9     GAVYAGYDVLDY

10    QVQLVQSGAEVKKPGSSVKVSCKASGYTFTNYWMHWVRQAPGQGLEWMGATY
      RGHSDTYYNQKFKGRVTITADKSTSTAYMELSSLRSEDTAVYYCTRGAVYAGYDV
      LDYWGQGTTVTVSS

11    QVQLVQSGAEVKKPGSSVKVSCKASGYTFTNYWMHWVRQAPGQGLEWMGATY
      RGHSDTYYNQKFKGRVTITADKSTSTAYMELSSLRSEDTAVYYCTRGAIYDGYDV
      LDNWGQGTLVTVSS

12    QVQLVESGGGVVQPGRSLRLSCAASGFKFSGYGMHWVRQAPGKGLEWVAVIWFD
      GSRKYYVDSVKGRFTISRDNSKNTLYLQMNSLRAEDTAVYYCARQMGYWHFGL
      WGRGTLVTVSS

13    DIQMTQSPSSLSASVGDRVTITCRASQGINNSLTWYQQKPGKAPKLLIYGASNRETG
      VPSRFSGSGSGTDFTLTISSLQPEDFATYYCQQWLKLPPTFGQGTKVEIK

14    DIQMTQSPSSLSASVGDRVTITCRASQSISNYLTWYQQKPGKAPKLLIYEASSRPSG
      VPSRFSGSGSGTDFTLTISSLQPEDFATYYCQQWSRLPVTFGQGTKVEIK

15    ERKSCVECPPCP

16    DIQMTQSPSSLSASVGDRVTITCSASQDISNYLNWYQQKPGKAPKLLIYYTSNLHSG
      VPSRFSGSGSGTDFTLTISSLQPEDFATYYCQQYRKLPWTFGQGTKLEIK

17    ASTKGPSVFPLAPSSKSTSGGTAALGCLVKDYFPEPVTVSWNSGALTSGVHTFPAV
      LQSSGLYSLSSVVTVPSSSLGTQTYICNVNHKPSNTKVDKRVEPKSCDKTHTCPPCP
      APELLGGPSVFLFPPKPKDTLMISRTPEVTCVVVDVSHEDPEVKFNWYVDGVEVHN
      AKTKPREEQYNSTYRVVSVLTVLHQDWLNGKEYKCKVSNKALPAPIEKTISKAKG
      QPREPQVYTLPPCREEMTKNQVSLWCLVKGFYPSDIAVEWESNGQPENNYKTTPP
      VLDSDGSFFLYSKLTVDKSRWQQGNVFSCSVMHEALHNHYTQKSLSLSPGK

18    ASTKGPSVFPLAPSSKSTSGGTAALGCLVKDYFPEPVTVSWNSGALTSGVHTFPAV
      LQSSGLYSLSSVVTVPSSSLGTQTYICNVNHKPSNTKVDKRVEPKSCDKTHTCPPCP
      APEFEGGPSVFLFPPKPKDTLMISRTPEVTCVVVDVSHEDPEVKFNWYVDGVEVHN
      AKTKPREEQYNSTYRVVSVLTVLHQDWLNGKEYKCKVSNKALPASIEKTISKAKG
      QPREPQVCTLPPSREEMTKNQVSLSCAVKGFYPSDIAVEWESNGQPENNYKTTPPV
      LDSDGSFFLVSKLTVDKSRWQQGNVFSCSVMHEALHNHYTQKSLSLSPGK

19    ASTKGPSVFPLAPSSKSTSGGTAALGCLVKDYFPEPVTVSWNSGALTSGVHTFPAV
      LQSSGLYSLSSVVTVPSSSLGTQTYICNVNHKPSNTKVDKRVEPKSCDKTHTCPPCP
      APEFEGGPSVFLFPPKPKDTLMISRTPEVTCVVVDVSHEDPEVKFNWYVDGVEVHN
      AKTKPREEQYNSTYRVVSVLTVLHQDWLNGKEYKCKVSNKALPASIEKTISKAKG
      QPREPQVYTLPPCREEMTKNQVSLWCLVKGFYPSDIAVEWESNGQPENNYKTTPP
      VLDSDGSFFLYSKLTVDKSRWQQGNVFSCSVMHEALHNHYTQKSLSLSPGK

20    RTVAAPSVFIFPPSDEQLKSGTASVVCLLNNFYPREAKVQWKVDNALQSGNSQESV
      TEQDSKDSTYSLSSTLTLSKADYEKHKVYACEVTHQGLSSPVTKSFNRGEC

21    GQPKAAPSVTLFPPSSEELQANKATLVCLISDFYPGAVTVAWKADSSPVKAGVETT
      TPSKQSNNKYAASSYLSLTPEQWKSHRSYSCQVTHEGSTVEKTVAPTECS

22    QDGNEEMGGITQTPYKVSISGTTVILTCPQYPGSEILWQHNDKNIGGDEDDKNIGSD
      EDHLSLKEFSELEQSGYYVCYPRGSKPEDANFYLYLRARVCENCMEMD

23    FKIPIEELEDRVFVNCNTSITWVEGTVGTLLSDITRLDLGKRILDPRGIYRCNGTDIYK
      DKESTVQVHYRMCQSCVELDPATVA

24    QDGNEEMGSITQTPYQVSISGTTVILTCSQHLGSEAQWQHNGKNKEDSGDRLFLPE
      FSEMEQSGYYVCYPRGSNPEDASHHLYLKARVCENCMEMD

25    FKIPVEELEDRVFVKCNTSVTWVEGTVGTLLTNNTRLDLGKRILDPRGIYRCNGTDI
      YKDKESAVQVHYRMCQNCVELDPATLA

-continued

| Sequence Listing | |
| --- | --- |
| SEQ ID NO | Amino Acid Sequence |

26  DDAENIEYKVSISGTSVELTCPLDSDENLKWEKNGQELPQKHDKHLVLQDFSEVED
    SGYYVCYTPASNKNTYLYLKARVCEYCVEVD

27  FKIQVTEYEDKVFVTCNTSVMHLDGTVEGWFAKNKTLNLGKGVLDPRGIYLCNGT
    EQLAKVVSSVQVHYRMCQNCVELDSGTMA

28  MLQMAGQCSQNEYFDSLLHACIPCQLRCSSNTPPLTCQRYCNASVTNSVKGTNA

29  MLQMARQCSQNEYFDSLLHDCKPCQLRCSSTPPLTCQRYCNASMTNSVKGMN

30  MAQQCFHSEYFDSLLHACKPCHLRCSNPPATCQPYCDPSVTSSVKGTYT

31  HHHHHH

32  PRGPTIKPCPPCKCPAPNLLGGPSVFIFPPPKIKDVLMISLSPIVTCVVVDVSEDDPDVQ
    ISWFVNNVEVHTAQTQTHREDYNSTLRVVSALPIQHQDWMSGKEFKCKVNNKDL
    PAPIERTISKPKGSVRAPQVYVLPPPEEEMTKKQVTLTCMVTDFMPEDIYVEWTNN
    GKTELNYKNTEPVLDSDGSYFMYSKLRVEKKNWVERNSYSCSVVHEGLHNHHTT
    KSFSRTPGK

33  EPKSSDKTHTCPPCPAPELLGGPSVFLFPPPKPKDTLMISRTPEVTCVVVDVSHEDPEV
    KFNWYVDGVEVHNAKTKPREEQYNSTYRVVSVLTVLHQDWLNGKEYKCKVSNK
    ALPAPIEKTISKAKGQPREPQVYTLPPCREEMTKNQVSLWCLVKGFYPSDIAVEWE
    SNGQPENNYKTTPPVLDSDGSFFLYSKLTVDKSRWQQGNVFSCSVMHEALHNHYT
    QKSLSLSPGK

34  EPKSSDKTHTCPPCPAPELLGGPSVFLFPPPKPKDTLMISRTPEVTCVVVDVSHEDPEV
    KFNWYVDGVEVHNAKTKPREEQYNSTYRVVSVLTVLHQDWLNGKEYKCKVSNK
    ALPAPIEKTISKAKGQPREPQVCTLPPSREEMTKNQVSLSCAVKGFYPSDIAVEWES
    NGQPENNYKTTPPVLDSDGSFFLVSKLTVDKSRWQQGNVFSCSVMHEALHNHYTQ
    KSLSLSPGK

35  ASTKGPSVFPLAPSSKSTSGGTAALGCLVKDYFPEPVTVSWNSGALTSGVHTFPAV
    LQSSGLYSLSSVVTVPSSSLGTQTYICNVNHKPSNTKVDKRVEPKSCDKTHTCPPCP
    APELLGGPSVFLFPPPKPKDTLMISRTPEVTCVVVDVSHEDPEVKFNWYVDGVEVHN
    AKTKPREEQYNSTYRVVSVLTVLHQDWLNGKEYKCKVSNKALPAPIEKTISKAKG
    QPREPQVYTLPPSREEMTKNQVSLTCLVKGFYPSDIAVEWESNGQPENNYKTTPPV
    LDSDGSFFLYSKLTVDKSRWQQGNVFSCSVMHEALHNHYTQKSLSLSPGK

36  ASTKGPSVFPLAPSSKSTSGGTAALGCLVKDYFPEPVTVSWNSGALTSGVHTFPAV
    LQSSGLYSLSSVVTVPSSSLGTQTYICNVNHKPSNTKVDKRVEPKSCDKTHTCPPCP
    APELLGGPSVFLFPPPKPKDTLMISRTPEVTCVVVDVSHEDPEVKFNWYVDGVEVHN
    AKTKPREEQYNSTYRVVSVLTVLHQDWLNGKEYKCKVSNKALPAPIEKTISKAKG
    QPREPQVCTLPPSREEMTKNQVSLSCAVKGFYPSDIAVEWESNGQPENNYKTTPPV
    LDSDGSFFLVSKLTVDKSRWQQGNVFSCSVMHEALHNHYTQKSLSLSPGK

37  ASTKGPSVFPLAPSSKSTSGGTAALGCLVKDYFPEPVTVSWNSGALTSGVHTFPAV
    LQSSGLYSLSSVVTVPSSSLGTQTYICNVNHKPSNTKVDKRVERKSCVECPPCPAPE
    FEGGPSVFLFPPPKPKDTLMISRTPEVTCVVVDVSHEDPEVKFNWYVDGVEVHNAK
    TKPREEQYNSTYRVVSVLTVLHQDWLNGKEYKCKVSNKALPASIEKTISKAKGQP
    REPQVYTLPPCREEMTKNQVSLWCLVKGFYPSDIAVEWESNGQPENNYKTTPPVL
    DSDGSFFLYSKLTVDKSRWQQGNVFSCSVMHEALHNHYTQKSLSLSPGK

38  ASTKGPSVFPLAPSSKSTSEGTAALGCLVKDYFPEPVTVSWNSGALTSGVHTFPAVL
    QSSGLYSLSSVVTVPSSSLGTQTYICNVDHKPSNTKVDKTVERKSCVECPPCPAPEF
    EGGPSVFLFPPPKPKDTLMISRTPEVTCVVVDVSQEDPEVQFNWYVDGVEVHNAKT
    KPREEQYNSTYRVVSVLTVLHQDWLNGKEYKCKVSNKALPASIEKTISKAKGQPR
    EPQVCTLPPSQEEMTKNQVSLSCAVKGFYPSDIAVEWESNGQPENNYKTTPPVLDS
    DGSFFLVSKLTVDKSRWQEGNVFSCSVMHEALHNHYTQKSLSLSPGK

39  QVQLVESGGGVVQPGRSLRLSCAASGFKFSGYGMHWVRQAPGKGLEWVAVIWFD
    GSRKYYVDSVKGRFTISRDNSKNTLYLQMNSLRAEDTAVYYCARQMGYWHFGL
    WGRGTLVTVSSASTKGPSVFPLAPSSKSTSGGTAALGCLVKDYFPEPVTVSWNSGA
    LTSGVHTFPAVLQSSGLYSLSSVVTVPSSSLGTQTYICNVNHKPSNTKVDKRVERKS
    CVECPPCPAPEFEGGPSVFLFPPPKPKDTLMISRTPEVTCVVVDVSHEDPEVKFNWYV
    DGVEVHNAKTKPREEQYNSTYRVVSVLTVLHQDWLNGKEYKCKVSNKALPASIE
    KTISKAKGQPREPQVYTLPPCREEMTKNQVSLWCLVKGFYPSDIAVEWESNGQPEN
    NYKTTPPVLDSDGSFFLYSKLTVDKSRWQQGNVFSCSVMHEALHNHYTQKSLSLS
    PGK

40  QVQLVQSGAEVKKPGSSVKVSCKASGYTFTNYWMHWVRQAPGQGLEWMGATY
    RGHSDTYYNQKFKGRVTITADKSTSTAYMELSSLRSEDTAVYYCTRGAVYAGYDV
    LDYWGQGTTVTVSSASTKGPSVFPLAPSSKSTSEGTAALGCLVKDYFPEPVTVSWN
    SGALTSGVHTFPAVLQSSGLYSLSSVVTVPSSSLGTQTYICNVDHKPSNTKVDKTVE
    RKSCVECPPCPAPEFEGGPSVFLFPPPKPKDTLMISRTPEVTCVVVDVSQEDPEVQFN

-continued

Sequence Listing

| SEQ ID NO | Amino Acid Sequence |
|---|---|

```
           WYVDGVEVHNAKTKPREEQYNSTYRVVSVLTVLHQDWLNGKEYKCKVSNKALP
           ASIEKTISKAKGQPREPQVCTLPPSQEEMTKNQVSLSCAVKGFYPSDIAVEWESNGQ
           PENNYKTTPPVLDSDGSFFLVSKLTVDKSRWQEGNVFSCSVMHEALHNHYTQKSL
           SLSPGK

41     DIQMTQSPSSLSASVGDRVTITCRASQSISNYLTWYQQKPGKAPKLLIYEASSRPSG
           VPSRFSGSGSGTDFTLTISSLQPEDFATYYCQQWSRLPVTFGQGTKVEIKRTVAAPS
           VFIFPPSDEQLKSGTASVVCLLNNFYPREAKVQWKVDNALQSGNSQESVTEQDSKD
           STYSLSSTLTLSKADYEKHKVYACEVTHQGLSSPVTKSFNRGEC

42     QVQLVESGGGVVQPGRSLRLSCAASGFKFSGYGMHWVRQAPGKGLEWVAVIWFD
           GSRKYYVDSVKGRFTISRDNSKNTLYLQMNSLRAEDTAVYYCARQMGYWHFGL
           WGRGTLVTVSSASTKGPSVFPLAPSSKSTSGGTAALGCLVKDYFPEPVTVSWNSGA
           LTSGVHTFPAVLQSSGLYSLSSVVTVPSSSLGTQTYICNVNHKPSNTKVDKRVEPKS
           CDKTHTCPPCPAPEFEGGPSVFLFPPKPKDTLMISRTPEVTCVVVDVSHEDPEVKFN
           WYVDGVEVHNAKTKPREEQYNSTYRVVSVLTVLHQDWLNGKEYKCKVSNKALP
           ASIEKTISKAKGQPREPQVYTLPPCREEMTKNQVSLWCLVKGFYPSDIAVEWESNG
           QPENNYKTTPPVLDSDGSFFLYSKLTVDKSRWQQGNVFSCSVMHEALHNHYTQKS
           LSLSPGK

43     QVQLVQSGAEVKKPGSSVKVSCKASGYTFTNYWMHWVRQAPGQGLEWMGATY
           RGHSDTYYNQKFKGRVTITADKSTSTAYMELSSLRSEDTAVYYCTRGAVYAGYDV
           LDYWGQGTTVTVSSASTKGPSVFPLAPSSKSTSGGTAALGCLVKDYFPEPVTVSWN
           SGALTSGVHTFPAVLQSSGLYSLSSVVTVPSSSLGTQTYICNVNHKPSNTKVDKRVE
           PKSCDKTHTCPPCPAPEFEGGPSVFLFPPKPKDTLMISRTPEVTCVVVDVSHEDPEV
           KFNWYVDGVEVHNAKTKPREEQYNSTYRVVSVLTVLHQDWLNGKEYKCKVSNK
           ALPASIEKTISKAKGQPREPQVCTLPPSREEMTKNQVSLSCAVKGFYPSDIAVEWES
           NGQPENNYKTTPPVLDSDGSFFLVSKLTVDKSRWQQGNVFSCSVMHEALHNHYTQ
           KSLSLSPGK
```

SEQUENCE DESCRIPTION

SEQ ID NO:1 shows the amino acid sequence of HCDR1 of the heavy chain variable region H10B7 of the anti-human CD3E monoclonal antibody H10B7+L1G10.

SEQ ID NO:2 shows the amino acid sequence of HCDR2 of the heavy chain variable region H10B7 of the anti-human CD3E monoclonal antibody H10B7+L1G10.

SEQ ID NO:3 shows the amino acid sequence of HCDR3 of the heavy chain variable region H1OB7 of the anti-human CD3E monoclonal antibody H10B7+L1G10.

SEQ ID NO:4 shows the amino acid sequence of LCDR1 of the light chain variable region L9B9.

SEQ ID NO:5 shows the amino acid sequence of LCDR2 of the light chain variable region L9B9.

SEQ ID NO:6 shows the amino acid sequence of LCDR3 of the light chain variable region L9B9.

SEQ ID NO:7 shows the amino acid sequence of HCDR1 of the heavy chain variable region mutant H13F1 of the anti-human BCMA monoclonal antibody C4.

SEQ ID NO:8 shows the amino acid sequence of HCDR2 of the heavy chain variable region mutant H13F1 of the anti-human BCMA monoclonal antibody C4.

SEQ ID NO:9 shows the amino acid sequence of HCDR3 of the heavy chain variable region mutant H13F1 of the anti-human BCMA monoclonal antibody C4.

SEQ ID NO: 10 shows the amino acid sequence of the heavy chain variable region mutant H13F1 of the anti-human BCMA monoclonal antibody C4.

SEQ ID NO: 11 shows the amino acid sequence of the heavy chain variable region C4VH of the anti-human BCMA monoclonal antibody C4.

SEQ ID NO: 12 shows the amino acid sequence of the heavy chain variable region Hl 0B7 of the anti-human CD3E monoclonal antibody H10B7+L1G10.

SEQ ID NO:13 shows the amino acid sequence of the light chain variable region L1 G10 of the anti-human CD3E monoclonal antibody H1 0B 7+L 1G10.

SEQ ID NO: 14 shows the amino acid sequence of the light chain variable region L9B9.

SEQ ID NO:15 shows the amino acid sequence of hinge region.

SEQ ID NO: 16 shows the amino acid sequence of the light chain variable region C4VK of the anti-human BCMA monoclonal antibody C4.

SEQ ID NO: 17 shows the amino acid sequence of the heavy chain constant region mutant IgG1K of human IgG1 subtype antibody.

SEQ ID NO: 18 shows the amino acid sequence of the heavy chain constant region mutant IgG1m3-H of human IgG1 subtype antibody.

SEQ ID NO: 19 shows the amino acid sequence of the heavy chain constant region mutant IgG1m3-K of human IgG1 subtype antibody.

SEQ ID NO:20 shows the amino acid sequence of the light chain constant region of human kappa (x) subtype.

SEQ ID NO:21 shows the amino acid sequence of the light chain constant region of human lambda (X) subtype.

SEQ ID NO:22 shows the amino acid sequence of the extracellular region of human CD3E.

SEQ ID NO:23 shows the amino acid sequence of the extracellular region of human CD3D.

SEQ ID NO:24 shows the amino acid sequence of the extracellular region of monkey CD3E.

SEQ ID NO:25 shows the amino acid sequence of the extracellular region of monkey CD3D.

SEQ ID NO: 26 shows the amino acid sequence of the extracellular region of mouse CD3E.

SEQ ID NO:27 shows the amino acid sequence of the extracellular region of mouse CD3D.

SEQ ID NO:28 shows the amino acid sequence of the extracellular region of human BCMA.

SEQ ID NO:29 shows the amino acid sequence of the extracellular region of monkey BCMA.

SEQ ID NO:30 shows the amino acid sequence of the extracellular region of mouse BCMA.

SEQ ID NO:31 shows the amino acid sequence of His tag.

SEQ ID NO:32 shows the amino acid sequence of Fc segment of mouse antibody IgG2a (mFc). SEQ ID NO:33 shows the amino acid sequence of the Fc mutant FcK of human IgG1 subtype of heterodimer.

SEQ ID NO:34 shows the amino acid sequence of the Fc mutant FcH of human IgG1 subtype of heterodimer.

SEQ ID NO: 35 shows the amino acid sequence of the heavy chain constant region of human IgG1 subtype antibody.

SEQ ID NO:36 shows the amino acid sequence of the heavy chain constant region mutant IgG1H of human IgG1 subtype antibody.

SEQ ID NO:37 shows the amino acid sequence of CD3 heavy chain constant region for GR1803.

SEQ ID NO:38 shows the amino acid sequence of BCMA heavy chain constant region for GR1803.

SEQ ID NO:39 shows the amino acid sequence of CD3 heavy chain variable region and heavy chain constant region for GR1803.

SEQ ID NO:40 shows the amino acid sequence of BCMA heavy chain variable region and heavy chain constant region for GR1803.

SEQ ID NO:41 shows the amino acid sequence of light chain variable region and light chain constant region for GR1803.

SEQ ID NO:42 shows the amino acid sequence of CD3 heavy chain variable region and heavy chain constant region for an exemplary bispecific antibody.

SEQ ID NO:43 shows the amino acid sequence of BCMA heavy chain variable region and heavy chain constant region for an exemplary bispecific antibody.

Various non-limiting embodiments are contemplated as described in the following paragraphs.

1. A bispecific antibody comprising a first arm and a second arm, wherein the first arm comprises a first antigen-binding portion against human CD3E, wherein the first arm comprises a heavy chain variable region comprising an amino acid sequence at least 80% identical to the amino acid sequence of SEQ ID NO: 12, a heavy chain constant region comprising an amino acid sequence at least 80% identical to the amino acid sequence of SEQ ID NO:37, a light chain variable region comprising an amino acid sequence at least 80% identical to the amino acid sequence of SEQ ID NO:14, and a light chain constant region comprising an amino acid sequence at least 80% identical to the amino acid sequence of SEQ ID NO:20, and and the second arm comprises a second antigen-binding portion against human BCMA, wherein the second arm comprises a heavy chain variable region comprising an amino acid sequence at least 80% identical to the amino acid sequence of SEQ ID NO:10, a heavy chain constant region comprising an amino acid sequence at least 80% identical to the amino acid sequence of SEQ ID NO:38, a light chain variable region comprising an amino acid sequence at least 80% identical to the amino acid sequence of SEQ ID NO:14, and a light chain constant region an amino acid sequence at least 80% identical to the amino acid sequence of SEQ ID NO: 20.

2. The bispecific antibody of embodiment 1, wherein the first arm comprises a heavy chain variable region comprising an amino acid sequence at least 85% identical, alternatively at least 88% identical, alternatively at least 90% identical, alternatively at least 91% identical, alternatively at least 92% identical, alternatively at least 93% identical, alternatively at least 94% identical, alternatively at least 95% identical, alternatively at least 96% identical, alternatively at least 97% identical, alternatively at least 98% identical, or alternatively at least 99% identical to the amino acid sequence of SEQ ID NO:12.

3. The bispecific antibody of embodiment 1 or embodiment 2, wherein the first arm comprises a heavy chain variable region comprising the amino acid sequence of SEQ ID NO: 12.

4. The bispecific antibody of any one of embodiments 1 to 3, wherein the first arm comprises a heavy chain constant region comprising an amino acid sequence at least 85% identical, alternatively at least 88% identical, alternatively at least 90% identical, alternatively at least 91% identical, alternatively at least 92% identical, alternatively at least 93% identical, alternatively at least 94% identical, alternatively at least 95% identical, alternatively at least 96% identical, alternatively at least 97% identical, alternatively at least 98% identical, or alternatively at least 99% identical to the amino acid sequence of SEQ ID NO:37.

5. The bispecific antibody of any one of embodiments 1 to 4, wherein the first arm comprises a heavy chain constant region comprising the amino acid sequence of SEQ ID NO: 37.

6. The bispecific antibody of any one of embodiments 1 to 5, wherein the second arm comprises a heavy chain variable region comprising an amino acid sequence at least 85% identical, alternatively at least 88% identical, alternatively at least 90% identical, alternatively at least 91% identical, alternatively at least 92% identical, alternatively at least 93% identical, alternatively at least 94% identical, alternatively at least 95% identical, alternatively at least 96% identical, alternatively at least 97% identical, alternatively at least 98% identical, or alternatively at least 99% identical to the amino acid sequence of SEQ ID NO:10.

7. The bispecific antibody of any one of embodiments 1 to 6, wherein the second arm comprises a heavy chain variable region comprising the amino acid sequence of SEQ ID NO: 10.

8. The bispecific antibody of any one of embodiments 1 to 7, wherein the second arm comprises a heavy chain constant region comprising an amino acid sequence at least 85% identical, alternatively at least 88% identical, alternatively at least 90% identical, alternatively at least 91% identical, alternatively at least 92% identical, alternatively at least 93% identical, alternatively at least 94% identical, alternatively at least 95% identical, alternatively at least 96% identical, alternatively at least 97% identical, alternatively at least 98% identical, or alternatively at least 99% identical to the amino acid sequence of SEQ ID NO:38.

9. The bispecific antibody of any one of embodiments 1 to 8, wherein the second arm comprises a heavy chain constant region comprising the amino acid sequence of SEQ ID NO: 38.

10. The bispecific antibody of any one of embodiments 1 to 9, wherein the first arm and/or the second arm comprises a light chain variable region comprising an amino acid sequence at least 85% identical, alternatively at least 88% identical, alternatively at least 90% identical, alternatively at least 91% identical, alternatively at least 92% identical, alternatively at least 93% identical, alternatively at least 94% identical, alternatively at least 95% identical, alternatively at least 96% identical, alternatively at least 97% identical, alternatively at least 98% identical, or alternatively at least 99% identical to the amino acid sequence of SEQ ID NO: 14.

11. The bispecific antibody of any one of embodiments 1 to 10, wherein the first arm and/or the second arm comprises a light chain variable region comprising the amino acid sequence of SEQ ID NO:14.

12. The bispecific antibody of any one of embodiments 1 to 11, wherein the first arm and/or the second arm comprises a light chain constant region comprising an amino acid sequence at least 85% identical, alternatively at least 88% identical, alternatively at least 90% identical, alternatively at least 91% identical, alternatively at least 92% identical, alternatively at least 93% identical, alternatively at least 94% identical, alternatively at least 95% identical, alternatively at least 96% identical, alternatively at least 97% identical, alternatively at least 98% identical, or alternatively at least 99% identical to the amino acid sequence of SEQ ID NO:20.

13. The bispecific antibody of any one of embodiments 1 to 12, wherein the first arm and/or the second arm comprises a light chain constant region comprising the amino acid sequence of SEQ ID NO:20.

14. A bispecific antibody comprising a first arm and a second arm, wherein the first arm comprises the amino acid sequences of SEQ ID NOs: 39 and 41 and the second arm comprises the amino acid sequences of SEQ ID NOs: 40 and 41.

15. The bispecific antibody of any one of embodiments 1 to 14, wherein the bispecific antibody has an isoelectric point between about 8.5 to about 9.5, alternatively about 9.0.

16. The bispecific antibody of any one of embodiments 1 to 15, wherein the HC (anti-BCMA) $N_{298}$/HC (anti-CD3) $N_{295}$ comprises at least one glycosylation modification.

17. The bispecific antibody of embodiment 16, wherein the main glycoform is A2G0F.

18. The bispecific antibody of embodiment 17, wherein the proportion of A2G0F glycoform is between about 73.0% and about 73.5%.

19. The bispecific antibody of any one of embodiments 1 to 18, wherein the affinity constant KD to CD3D & CD3E antigen is between about $1.261 \times 10^{-7}$M and about $2.412 \times 10^{-7}$M.

20. The bispecific antibody of any one of embodiments 1 to 19, wherein the affinity constant KD to BCMA-his antigen is between about $4.880 \times 10^{-10}$ M and about $5.405 \times 10^{-10}$ M.

21. The bispecific antibody of any one of embodiments 1 to 20, wherein the bispecific antibody can bind to FcRn under acidic conditions, the affinity constant KD is between about $7.917 \times 10^{-5}$ M and $9.243 \times 10^{-5}$ M, and the $EC_{50}$ value is between about 2.405 µg/ml and about 2.455 µg/ml.

22. The bispecific antibody of embodiment 21, wherein the bispecific antibody has an affinity constant KD was $9.243 \times 10^{-5}$ M and a $EC_{50}$ value of 2.405 µg/ml.

23. The bispecific antibody of embodiment 21, wherein the bispecific antibody has affinity constant KD of $7.917 \times 10^{-5}$ M and a $EC_{50}$ value of 2.455 µg/ml.

24 The bispecific antibody of any one of embodiments 1 to 23, wherein the bispecific antibody can bind to CD3D & CD3E and BCMA-his antigen simultaneously and the binding activity $EC_{50}$ is between about 3.224 µg/ml and about 8.183 µg/ml.

25. The bispecific antibody of any one of embodiments 1 to 24, wherein the bispecific antibody can engage T cells with BCMA positive tumor cells in vitro and activate T cells and the binding activity $EC_{50}$ is between about 0.045 µg/ml and about 0.049 µg/ml.

26. The bispecific antibody of any one of embodiments 1 to 25, wherein the bispecific antibody has a melting temperature of about 61° C.

27. The bispecific antibody of embodiment 26, wherein the bispecific antibody has good thermal stability.

28. The bispecific antibody of any one of embodiments 1 to 27, wherein deamidation modification the bispecific antibody occurs at:

HC (anti-BCMA) $N_{316}$/HC (anti-CD3) $N_{313}$ at a proportion of 2.2%-2.3%,

HC (anti-BCMA) $N_{362}$ at a proportion of 1.2%, $N_{385}$ at a proportion of 1.5%, HC (anti-BCMA) $N_{390}$/HC (anti-CD3) $N_{387}$ at a proportion of 6.1-6.2%, and/or HC (anti-BCMA) $N_{435}$/HC (anti-CD3) $N_{437}$ at a proportion of 2.6-2.7%.

29. The bispecific antibody of any one of embodiments 1 to 28, wherein the oxidative modification occurs at:

LC $M_4$ at a proportion of 0.1%,

HC (anti-BCMA) $M_{34}$ at a proportion of 0.5%-0.6%, $_{162}$ of heavy chain at a proportion of 0.3%, HC (anti-BCMA) $M_{253}$/HC (anti-CD3) $M_{250}$ at a proportion of 4.2%-5.1%, HC (anti-BCMA) $M_{429}$ at a proportion of 0.8%-0.9%, HC (anti-CD3) $M_{100}$ at a proportion of 9.5%-11.4%, and/or HC (anti-CD3) $M_{426}$ at a proportion of 0.3%.

30. The bispecific antibody of any one of embodiments 1 to 29, wherein the bispecific antibody can T cells by specifically binding to CD3 on the surface of T cells and BCMA on the surface of tumor cells.

31. A pharmaceutical compositions comprising the bispecific antibody of any one of embodiments 1 to 30 and a pharmaceutically acceptable carrier or excipient.

Although the present application has been described in detail with reference to the general description and specific embodiments, it will be apparent to those skilled in the art that modifications or improvements can be made to the present invention on the basis of the present application. Accordingly, all these modifications or improvements made without departing from the spirit of the present application will fall within the scope of the invention as claimed.

The invention claimed is:

1. A bispecific antibody comprising a first arm and a second arm, wherein the first arm comprises a first antigen-binding portion against human CD3E, wherein the first arm comprises a heavy chain variable region comprising the amino acid sequence of SEQ ID NO:12, a heavy chain constant region comprising the amino acid sequence of SEQ ID NO:37, a light chain variable region comprising the amino acid sequence of SEQ ID NO: 14, and a light chain constant region comprising the amino acid sequence of SEQ ID NO:20, and and wherein the second arm comprises a second antigen-binding portion against human BCMA, wherein the second arm comprises a heavy chain variable region comprising the amino acid sequence of SEQ ID NO:10, a heavy chain constant region comprising the amino acid sequence of SEQ ID NO:38, a light chain variable region comprising the amino acid sequence of SEQ ID NO:14, and a light chain constant region comprising the amino acid sequence of SEQ ID NO: 20.

2. The bispecific antibody of claim 1, wherein the bispecific antibody is an IgG1 antibody comprising two heavy chain constant regions having the same hinge region, wherein the amino acid sequence of the hinge region comprises the amino acid sequence of SEQ ID NO: 15.

3. The bispecific antibody of claim 1, wherein
the first antigen-binding portion comprises a Fab fragment and the second antigen-binding portion comprises a Fab fragment.

4. The bispecific antibody of claim 1, wherein the bispecific antibody has an isoelectric point between about 8.5 to about 9.5.

5. The bispecific antibody of claim 1, wherein the HC (anti-BCMA) $N_{298}$/HC (anti-CD3) $N_{295}$ comprises at least one glycosylation modification, wherein the main glycoform is A2G0F.

6. The bispecific antibody of claim 5, wherein the proportion of A2G0F glycoform is between about 73.0% and about 73.5%.

7. The bispecific antibody of claim 1, wherein the affinity constant KD to CD3D & CD3E antigen is between about $1.261 \times 10^{-7}$M and about $2.412 \times 10^{-7}$M; and/or
the affinity constant KD to BCMA-his antigen is between about $4.880 \times 10^{-10}$ M and about $5.405 \times 10^{-10}$ M.

8. The bispecific antibody of claim 1, wherein the bispecific antibody can bind to FcRn under acidic conditions, wherein the affinity constant KD is between about $7.917 \times 10^{-5}$ M and $9.243 \times 10^{-5}$ M, and the $EC_{50}$ value is between about 2.405 µg/ml and about 2.455 µg/ml.

9. The bispecific antibody of claim 8, wherein the bispecific antibody has an affinity constant KD of $9.243 \times 10^{-5}$ M and a $EC_{50}$ value of 2.405 µg/ml; and/or
the bispecific antibody has affinity constant KD of $7.917 \times 10^{-5}$ M and a $EC_{50}$ value of 2.455 µg/ml.

10. The bispecific antibody of claim 1, wherein the bispecific antibody can bind to CD3D & CD3E and BCMA-his antigen simultaneously and the binding activity $EC_{50}$ is between about 3.224 µg/ml and about 8.183 µg/ml; and/or wherein the bispecific antibody can engage T cells with BCMA positive tumor cells in vitro and activate T cells and the binding activity $EC_{50}$ is between about 0.045 µg/ml and about 0.049 µg/ml.

11. The bispecific antibody of claim 1, wherein the bispecific antibody has a melting temperature of about 61° C.

12. The bispecific antibody of claim 1, wherein deamidation modification occurs at:

HC (anti-BCMA) $N_{316}$/HC (anti-CD3) $N_{313}$ at a proportion of 2.2%-2.3%,

HC (anti-BCMA) $N_{362}$ at a proportion of 1.2%, $N_{385}$ at a proportion of 1.5%, HC (anti-BCMA) $N_{390}$/HC (anti-CD3) $N_{387}$ at a proportion of 6.1-6.2%, and/or HC (anti-BCMA) $N_{435}$/HC (anti-CD3) $N_{437}$ at a proportion of 2.6-2.7%;

and/or wherein oxidative modification occurs at:

LC $M_4$ at a proportion of 0.1%,

HC (anti-BCMA) $M_{34}$ at a proportion of 0.5%-0.6%, $_{162}$ of heavy chain at a proportion of 0.3%, HC (anti-BCMA) $M_{253}$/HC (anti-CD3) $M_{250}$ at a proportion of 4.2%-5.1%, HC (anti-BCMA) $M_{429}$ at a proportion of 0.8%-0.9%, HC (anti-CD3) $M_{100}$ at a proportion of 9.5%-11.4%, and/or HC (anti-CD3) $M_{426}$ at a proportion of 0.3%.

13. The bispecific antibody of claim 1, wherein the bispecific antibody can bind to T cells by specifically binding to CD3 on the surface of T cells and BCMA on the surface of tumor cells.

14. A pharmaceutical compositions comprising the bispecific antibody claim 1 and a pharmaceutically acceptable carrier or excipient.

15. A bispecific antibody comprising a first arm and a second arm, wherein the first arm comprises the amino acid sequences of SEQ ID NOs: 39 and 41 and the second arm comprises the amino acid sequences of SEQ ID NOs: 40 and 41.

16. The bispecific antibody of claim 15, wherein the bispecific antibody is an IgG1 antibody comprising two heavy chain constant regions having the same hinge region, wherein the amino acid sequence of the hinge region comprises the amino acid sequence of SEQ ID NO: 15.

17. The bispecific antibody of claim 15, wherein the bispecific antibody has an isoelectric point between about 8.5 to about 9.5.

18. The bispecific antibody of claim 15, wherein the HC (anti-BCMA) $N_{298}$/HC (anti-CD3) $N_{295}$ comprises at least one glycosylation modification, wherein the main glycoform is A2G0F.

19. The bispecific antibody of claim 18, wherein the proportion of A2G0F glycoform is between about 73.0% and about 73.5%.

20. The bispecific antibody of claim 15, wherein the affinity constant KD to CD3D & CD3E antigen is between about $1.261\times10^{-7}$ M and about $2.412\times10^{-7}$ M; and/or the affinity constant KD to BCMA-his antigen is between about $4.880\times10^{-10}$ M and about $5.405\times10^{-10}$ M.

56

21. The bispecific antibody of claim 15, wherein the bispecific antibody can bind to FcRn under acidic conditions, wherein the affinity constant KD is between about $7.917\times10^{-5}$ M and $9.243\times10^{-5}$ M, and the $EC_{50}$ value is between about 2.405 μg/ml and about 2.455 μg/ml.

22. The bispecific antibody of claim 21, wherein the bispecific antibody has an affinity constant KD of $9.243\times10^{-5}$ M and a $EC_{50}$ value of 2.405 μg/ml; and/or the bispecific antibody has affinity constant KD of $7.917\times10^{-5}$ M and a $EC_{50}$ value of 2.455 μg/ml.

23. The bispecific antibody of claim 15, wherein the bispecific antibody can bind to CD3D & CD3E and BCMA-his antigen simultaneously and the binding activity $EC_{50}$ is between about 3.224 μg/ml and about 8.183 μg/ml; and/or wherein the bispecific antibody can engage T cells with BCMA positive tumor cells in vitro and activate T cells and the binding activity $EC_{50}$ is between about 0.045 μg/ml and about 0.049 μg/ml.

24. The bispecific antibody of claim 15, wherein the bispecific antibody has a melting temperature of about 61° C.

25. The bispecific antibody of claim 15, wherein deamidation modification occurs at:

HC (anti-BCMA) $N_{316}$/HC (anti-CD3) $N_{313}$ at a proportion of 2.2%-2.3%,

HC (anti-BCMA) $N_{362}$ at a proportion of 1.2%, $N_{385}$ at a proportion of 1.5%, HC (anti-BCMA) $N_{390}$/HC (anti-CD3) $N_{387}$ at a proportion of 6.1-6.2%, and/or HC (anti-BCMA) $N_{435}$/HC (anti-CD3) $N_{437}$ at a proportion of 2.6-2.7%;

and/or wherein oxidative modification occurs at:

LC $M_4$ at a proportion of 0.1%,

HC (anti-BCMA) $M_{34}$ at a proportion of 0.5%-0.6%, $_{162}$ of heavy chain at a proportion of 0.3%, HC (anti-BCMA) $M_{253}$/HC (anti-CD3) $M_{250}$ at a proportion of 4.2%-5.1%, HC (anti-BCMA) $M_{429}$ at a proportion of 0.8%-0.9%, HC (anti-CD3) $M_{100}$ at a proportion of 9.5%-11.4%, and/or HC (anti-CD3) $M_{426}$ at a proportion of 0.3%.

26. The bispecific antibody of claim 15, wherein the bispecific antibody can bind to T cells by specifically binding to CD3 on the surface of T cells and BCMA on the surface of tumor cells.

27. A pharmaceutical composition comprising the bispecific antibody claim 15 and a pharmaceutically acceptable carrier or excipient.

* * * * *